US007316907B2

(12) United States Patent
Yu et al.

(10) Patent No.: US 7,316,907 B2
(45) Date of Patent: Jan. 8, 2008

(54) 14-3-3 ZETA OVER-EXPRESSION AS A POOR PROGNOSIS FACTOR, AND A THERAPEUTIC TARGET IN MULTIPLE CANCER TYPES

(75) Inventors: Dihua Yu, Houston, TX (US); Jun Yao, Chestnut Hill, MA (US); Christopher L. Neal, Houston, TX (US); Wentao Yang, Shanghai (CN); Xiaoyan Zhou, Shanghai (CN); Raphael E. Pollock, Houston, TX (US); Mien-Chie Hung, Houston, TX (US); Jun Yang, Houston, TX (US); Ping Li, Houston, TX (US); Nina T. Nguyen, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 49 days.

(21) Appl. No.: 10/938,387

(22) Filed: Sep. 10, 2004

(65) Prior Publication Data

US 2005/0148532 A1 Jul. 7, 2005

Related U.S. Application Data

(60) Provisional application No. 60/501,786, filed on Sep. 10, 2003.

(51) Int. Cl.
*G01N 33/53* (2006.01)
*G01N 33/574* (2006.01)
(52) U.S. Cl. ..................................... 435/7.1; 435/7.23
(58) Field of Classification Search ................. 435/7.1
See application file for complete search history.

(56) References Cited

U.S. PATENT DOCUMENTS

| | | | | |
|---|---|---|---|---|
| 4,578,770 A | 3/1986 | Mitani | ....................... | 364/571 |
| 4,596,792 A | 6/1986 | Vyas | ............................ | 514/21 |
| 4,599,230 A | 7/1986 | Milich et al. | ................. | 424/89 |
| 4,599,231 A | 7/1986 | Milich et al. | ................. | 424/89 |
| 4,601,903 A | 7/1986 | Frasch | ........................ | 424/92 |
| 4,608,251 A | 8/1986 | Mia | ............................ | 424/85 |
| 2003/0211624 A1* | 11/2003 | Goldknopf et al. | ........... | 436/86 |

OTHER PUBLICATIONS

Yang et al (Molec. Parmacol., 2002, 61:269-276).*
Tockman et al (Cancer Res., 1992, 52:2711s-2718s).*
Alberts et al. (Molecular Biology of the Cell, 3rd edition, 1994, p. 465).*
Lewin, B. (Genes VI, Oxford University Press, Inc., NY, Chapter 29, 1997).*
Fu et al (EMBO Journal, 1996, vol. 15, pp. 4392-4401).*
Mallampalli et al. (Biochem. J. vol. 318, 1996, pp. 333-341).*
Dermer (Bio/Technology, 1994, 12:320).*
Aitken et al., "14-3-3 proteins in cell regulation," 30(4):351-360, 2002.
Aitken et al., "14-3-3 proteins: a highly conserved, widespread family of eukaryotic proteins," *Trends Biochem Sci*, 17:498-501, 1992.
Aitken et al., "Kinase and neurotransmitters," *Nature*, 344(6267):594, 1990.
Aitken, "14-3-3 and its possible role in coordinating multiple signaling pathways," *Trends Cell Biol*, 6(9):341-347, 1996.
Albertson, "Profiling breast cancer by array CGH," *Breast Cancer Research and Treatment*, 78:289-298, 2003.
Ali et al., "Amplification of c-erbB-2 and aggressive human breast tumors?" *Science*, 240:1795-1798, 1988.
Bonnefoy-Berard et al., "Association of phosphatidylinositol 3-kinase (PI3-K) with 14-3-3 proteins," abstract #4069, *The 9th International Congress of Immunology*, San Francisco, CA, Jul. 23-29, 1995.
Bonnefoy-Bernard, "Inhibition of phosphatidylinositol 3-kinase activity by associateion with 14-3-3 proteins in T cells," *Proc. Natl. Acad. Sci., USA*, 92:10142-10146, 1995.
Brunet et al., "Akt promotes cell survival by phosphorylating and inhibiting a forkhead transcription factor," *Cell*, 96(6):857-868, 1999.
Cantley, "The phosphoinositide 3-kinase pathway," *Science*, 296:1655-1657, 2002.
Chan et al., "Modulation of the $Ca^{2+}$-activated $Cl^-$ channel by 14-3-3ε," *Biochem Biophys Res Commun*, 270(2):581-587, 2000.
De Valck et al., "A20 inhibits NF-κB activation independently of binding to 14-3-3 proteins," *Biochem Biophys Res Commun*, 238(2):590-594, 1997.
Ferguson et al., "High frequency of hypermethylation at the 14-3-3 δ locus leads to gene silencing in breast cancer," *Proc. Natl. Acad. Sci., USA*, 97(11):6049-6054, 2000.
Fodor et al., "A pancreatic exocrine cell factor and AP4 binding overlapping sites in the amylase 2A enhancer," *Biochemistry*, 30(33):8102-8108, 1991.
Fry et al., "A specific inhibitor of the epidermal growth factor receptor tyrosine kinase," *Science*, 265(5175):1093-1095, 1994.
Guthridge et al., "Site-specific serine phosphorylation of the IL-3 receptor is required for hemopoietic cell survival," *Mol Cell*, 6(1):99-108, 2000.
Hacia et al., "Detection of heterozygous mutations in BRCA1 using high density oligonucleotide arrays and two-colour fluorescence analysis," *Nature Genet*, 14:441-449, 1996.

(Continued)

*Primary Examiner*—Misook Yu
*Assistant Examiner*—Sean E Aeder
(74) *Attorney, Agent, or Firm*—Fulbright & Jaworski L.L.P.

(57) ABSTRACT

Methods of determining prognosis in a subject with a hyperproliferative disease, including determining expression and/or function of 14-3-3 zeta in the subject, are disclosed. Also disclosed are methods of making a pharmaceutical agent that modulates apoptosis, including the steps of obtaining one or more candidate, testing the one or more candidate substances to determine their ability to modulate the expression and/or function of 14-3-3 zeta, selecting a candidate substance determined to modulate the expression and/or function of 14-3-3 zeta, and making a pharmaceutical composition that includes the selected candidate substance. In addition, methods of treating a subject with a hyperproliferative disease, including making a pharmaceutical agent by the methods set forth herein, and administering the pharmaceutical agent to a subject, are disclosed. The hyperproliferative disease can be cancer, such as breast cancer.

18 Claims, 5 Drawing Sheets

OTHER PUBLICATIONS

Hermeking et al., "14-3-3σ is a p53-regulated inhibitor of G2/M progression," *Mol Cell*, 1(1):3-11, 1997.

Ichimura et al., "Molecular cloning of cDNA coding for brain-specific 14-3-3 protein, a protein kinase-dependent activator of tyrosine and tryptophan hydroxylases," *Proc. Natl. Acad. Sci.*, USA, 85(19):7084-7088, 1988.

Ichimura et al., "Widespread distribution of the 14-3-3 protein in vertebrate brains and bovine tissues: correlation with the distributions of calcium-dependent protein kinases," *J. Neurochem*, 56(4):1449-1451, 1991.

Isobe et al., "Distinct forms of the protein kinase-dependent activator of tyrosine tryptophane hydroxylases," *J. Mol Biol*, 217(1):125-132, 1991.

Kallioniemi et al., "Comparative genomic hybridization for molecular cytogenetic analysis of solid tumors," *Science*, 258(5083):818-821, 1992.

Laronga et al., "Association of the cyclin-dependent kinases and 14-3-3 sigma negatively regulates cell cycle progression," *J. Biol. Chem.*, 275(30):23106-23112, 2000.

Liu et al., "Activation-modulated association of 14-3-3 proteins with Cbl in T cells," *J. Biol. Chem.*, 271(24):14591-14595, 1996.

Liu et al., "Crystal structure of the zeta isoform of the 14-3-3 protein," *Nature*, 376(6536):191-194, 1995.

Masters and Fu, "14-3-3 proteins mediate and essential anti-apoptotic signal," *J. Biol. Chem.*, 276(48):45193-45200, 2001.

Moore and Perez, "Specific acidic proteins of the nervous system," In: *Physiological and biochemical aspects of nervous integration*, Carlson (Ed.,) 343-359, Prentice-Hall, NJ, 1967.

Munday et al., "Phosphoinositide 3-kinase forms a complex with platelet membrane glycoprotein Ib-IX-V complex and 14-3-3," *Blood*, 96(2):577-584, 2000.

Munday et al., "The phosphoinositide 3-kinase forms a complex with platelet membrane glycoprotein IB-IX-V complex and 14-3-3 zeta," *Cell Biology International*, 24(12):981, 2000.

Pease et al., "Light-generated oligonucleotide arrays for rapid DNA sequence analysis," *Proc. Natl. Acad. Sci. USA*, 91:5022-5026, 1994.

Rittinger et al., "Structural analysis of 14-3-3 phosphopeptide complexes identifies a dual role for the nuclear export signal of 14-3-3 in ligand binding," *Mol. Cell*, 4:153-166, 1999.

Rogers et al., "Molecular prognostic indicators in breast cancer," *Eur. J. Surg. Oncol.*, 28(5):467-478, 2002.

Rosenquist et al., "Evolution of the 14-3-3 protein family: does the large number of isoforms in multicellular organisms reflect functional specificity," *J. Mol. Evol.*, 51(5):446-458, 2000.

Shin et al., "Multiple isoforms of the regulatory subunit for phosphatidylinositol 3-kinase (P3-kinase) are expressed in neurons in the rat brain," *Biochem. Biophys. Res. Commun.*, 246(2):313-319, 1998.

Shoemaker et al., "Quantitative phenotypic analysis of yeast deletion mutants using a highly parallel molecular bar-coding strategy," *Nature Genet.*, 14:450-456, 1996.

Sladeczek et al., "The Cdk-like protein PCTAIRE-1 from mouse brain associates with p11 and 14-3-3 proteins," *Mol Gen Genet*, 254:571-577, 1997.

Slamon et al., "Studies of the HER-2/neu proto-oncogene in human breast and ovarian cancer," *Science*, 244:707-712, 1989.

Toker et al., "Protein kinase C inhibitor proteins: purification from sheep brain and sequence similarity to lipocortins and 14-3-3 protein," *Eur. J. Biochem.*, 191(2):421-429, 1990.

Veltman et al., "Array-based comparative genomic hybridization for genome-wide screening of DNA copy number in bladder tumors," *Cancer Res.*, 63:2872-2880, 2003.

Vercoutter-Edouart et al., "Proteomic analysis reveals that 14-3-3σ is down-regulated in human breast cancer cells," *Cancer Res.*, 61(1):76-80, 2001.

Vivanco and Sawyers, "The phosphatidylinositol 3-kinase-AKT pathway in human cancer," *Nat. Rev. Cancer*, 2:489-501, 2002.

Wang and Shakes, "Molecular evolution of the 14-3-3 protein family," *J. Mol. Evol.*, 43(4):384-398, 1996.

Watanabe et al., "Molecular cloning of cDNA to rat 14-3-3η chain polypeptide and the neuronal expression of the mRNA in the central nervous system," *Brain Res. Mol. Brain Res.*, 10(2):151-158, 1991.

Welch and Wei, "Genetic and epigenetic regulation of human breast cancer progression and metastasis," *Endocrine-Related Cancer*, 5:155-197, 1998.

Xiang et al., "14-3-3 facilitates insulin-stimulated intracellular trafficking of insulin receptor substrate 1,"*Molecular Endocrinology*, 16(3):552-562, 2002.

Xiao et al., "Structure of a 14-3-3 protein and implications for coordination of multiple signalling pathways," *Nature*, 376(6536):188-191, 1995.

Yaffe, "How do 14-3-3- proteins work? Gatekeeper phosphorylation and the molecular anvil hypothesis," *FEBS Lett.*, 513(1):53-57, 2002.

Yang et al., "Apolipoprotein B mRNA editing and the reduction in synthesis and secretion of the atherogenic risk factor, apolipoprotein B100 can be effectively targeted through TAT-mediated protein transduction," *Molec. Pharmacol.*, 61:269-276, 2002.

Zha et al., "Serine phosphorylation of death agonist BAD in response to survival factor results in binding to 14-3-3 not BCL-$X_L$," *Cell*, 87(4):619-628, 1996.

Zhang et al., "Suppression of apoptosis signal-regulating kinase 1-induced cell death by 14-3-3 proteins," *Proc. Natl. Acad. Sci. USA*, 96(15):8511-8515, 1999.

* cited by examiner

A.

B.

C.

D.

SEQUENCE LISTING

```
<160> NUMBER OF SEQ ID NOS: 4

<210> SEQ ID NO 1
<211> LENGTH: 245
<212> TYPE: PRT
<213> ORGANISM: Homo sapiens

<400> SEQUENCE: 1

Met Asp Lys Asn Glu Leu Val Gln Lys Ala Lys Leu Ala Glu Gln Ala
 1               5                  10                  15

Glu Arg Tyr Asp Asp Met Ala Ala Cys Met Lys Ser Val Thr Glu Gln
            20                  25                  30

Gly Ala Glu Leu Ser Asn Glu Glu Arg Asn Leu Leu Ser Val Ala Tyr
        35                  40                  45
```

```
Lys Asn Val Val Gly Ala Arg Arg Ser Ser Trp Arg Val Ser Ser
     50                  55                  60
Ile Glu Gln Lys Thr Glu Gly Ala Glu Lys Lys Gln Gln Met Ala Arg
 65                  70                  75                  80
Glu Tyr Arg Glu Lys Ile Glu Thr Glu Leu Arg Asp Ile Cys Asn Asp
                 85                  90                  95
Val Leu Ser Leu Leu Glu Lys Phe Leu Ile Pro Asn Ala Ser Gln Ala
            100                 105                 110
Glu Ser Lys Val Phe Tyr Leu Lys Met Lys Gly Asp Tyr Tyr Arg Tyr
            115                 120                 125
Leu Ala Glu Val Ala Ala Gly Asp Asp Lys Lys Gly Ile Val Asp Gln
130                 135                 140
Ser Gln Gln Ala Tyr Gln Glu Ala Phe Glu Ile Ser Lys Lys Glu Met
145                 150                 155                 160
Gln Pro Thr His Pro Ile Arg Leu Gly Leu Ala Leu Asn Phe Ser Val
                165                 170                 175
Phe Tyr Tyr Glu Ile Leu Asn Ser Pro Glu Lys Ala Cys Ser Leu Ala
            180                 185                 190
Lys Thr Ala Phe Asp Glu Ala Ile Ala Glu Leu Asp Thr Leu Ser Glu
            195                 200                 205
Glu Ser Tyr Lys Asp Ser Thr Leu Ile Met Gln Leu Leu Arg Asp Asn
210                 215                 220
Leu Thr Leu Trp Thr Ser Asp Thr Gln Gly Asp Glu Ala Glu Ala Gly
225                 230                 235                 240
Glu Gly Gly Glu Asn
                245

<210> SEQ ID NO 2
<211> LENGTH: 2834
<212> TYPE: DNA
<213> ORGANISM: Homo sapiens

<400> SEQUENCE: 2
gcccactccc accgccagct ggaaccctgg ggactacgac gtccctcaaa ccttgcttct      60
aggagataaa aagaacatcc agtcatggat aaaaatgagc tggttcagaa ggccaaactg     120
gccgagcagg ctgagcgata tgatgacatg gcagcctgca tgaagtctgt aactgagcaa     180
ggagctgaat tatccaatga ggagaggaat cttctctcag ttgcttataa aaatgttgta     240
ggagcccgta ggtcatcttg gagggtcgtc tcaagtattg aacaaaagac ggaaggtgct     300
gagaaaaaac agcagatggc tcgagaatac agagagaaaa ttgagacgga gctaagagat     360
atctgcaatg atgtactgtc tcttttggaa aagttcttga tccccaatgc ttcacaagca     420
gagagcaaag tcttctattt gaaaatgaaa ggagattact accgttactt ggctgaggtt     480
gccgctggtg atgacaagaa agggattgtc gatcagtcac aacaagcata ccaagaagct     540
tttgaaatca gcaaaaggga atgcaaccaa cacatcctat cagactgggt ctggcccctt     600
aacttctctg tgttctatta tgagattctg aactccccag agaaagcctg ctctcttgca     660
aagacagctt ttgatgaagc cattgctgaa cttgatacat aagtgaaga gtcatacaaa     720 gacagcacgc taataatgca attactgaga acaacttga cattgtggac atcggatacc     780
caaggagacg aagctgaagc aggagaagga ggggaaaatt aaccggcctt ccaacttttg     840
tctgcctcat tctaaaattt acacagtaga ccatttgtca tccatgctgt cccacaaata     900
gttttttgtt tacgatttat gacaggttta tgttacttct atttgaattt ctatatttcc     960
```

-continued

```
catgtggttt ttatgtttaa tattagggga gtagagccag ttaacattta gggagttatc    1020
tgttttcatc ttgaggtggc caatatgggg atgtggaatt tttatacaag ttataagtgt    1080
ttggcatagt acttttggta cattgtggct tcaaaagggc cagtgtaaaa ctgcttccat    1140
gtctaagcaa agaaaactgc ctacatactg gtttgtcctg gcggggaata aagggatca    1200 ttggttccag tcacaggtgt agtaattgtg ggtactttaa ggtttggagc acttacaagg    1260
ctgtggtaga atcataccc atggatacca catattaaac catgtatatc tgtggaatac    1320
tcaatgtgta ccctttgac tacagctgca gaagtgttcc tttagacaaa gttgtgaccc    1380
attttactct ggataagggc agaaacggtt cacattccat tatttgtaaa gttacctgct    1440
gttagctttc attatttttg ctacactcat tttatttgta tttaaatgtt ttaggcaacc    1500
taagaacaaa tgtaaaagta agatgcagg aaaaatgaat tgcttggtat tcattacttc    1560
atgtatatca agcacagcag taaaacaaaa acccatgtat ttaactttt tttaggattt    1620 ttgcttttgt gatttttttt tttttttttt gatacttgcc taacatgcat gtgctgtaaa    1680
aatagttaac agggaaataa cttgagatga tggctagctt tgtttaatgt cttatgaaat    1740
tttcatgaac aatccaagca taattgttaa gaacacgtgt attaaattca tgtaagtgga    1800
ataaagtttt tatgaatgga ctttcaact actttctcta cagcttttca tgtaaattag    1860
tcttggttct gaaacttctc taaggaaat tgtacatttt ttgaaattta ttccttattc    1920
cctcttggca gctaatgggc tcttaccaag tttaaacaca aaatttatca taacaaaaat    1980
actactaata taactactgt ttccatgtcc catgatcccc tctcttcctc cccaccctga    2040
aaaaaatgag ttcctatttt ttctgggaga ggggggatt gattagaaaa aaatgtagtg    2100
tgttccattt aaaattttgg catatggcat tttctaactt aggaagccac aatgttcttg    2160
gcccatcatg acattgggta gcattaactg taagttttgt gcttccaaat cacttttgg    2220 ttttttaagaa tttcttgata ctcttatagc ctgccttcaa ttttgatcct ttattctttc    2280
tatttgtcag gtgcacaaga ttaccttcct gttttagcct tctgtcttgt caccaaccat    2340
tcttacttgg tggccatgta cttggaaaaa ggccgcatga tctttctggc tccactcagt    2400
gtctaaggca ccctgcttcc tttgcttgca tcccacagac tatttccctc atcctattta    2460
ctgcagcaaa tctctcctta gttgatgaga ctgtgtttat ctcccttaa aaccctacct    2520 atcctgaatg gtctgtcatt gtctgccttt aaaatccttc ctctttcttc ctcctctatt    2580
ctctaaataa tgatggggct aagttatacc caaagctcac tttacaaaat atttcctcag    2640
tactttgcag aaaacaccaa acaaaaatgc cattttaaaa aaggtgtatt ttttcttta    2700 gaatgtaagc tcctcaagag cagggacaat gttttctgta tgttctattg tgcctagtac    2760
actgtaaatg ctcaataaat attgatgatg ggaggcagtg agtcttgatg ataagggtga    2820
gaaactgaaa tccc                                                     2834
```

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic Primer

<400> SEQUENCE: 3
aaaguucuug auccccaaug c    21

```
<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence:  Synthetic
      Primer

<400> SEQUENCE: 4
cagucgcguu ugcgacugg                                                    19
```

14-3-3 ZETA OVER-EXPRESSION AS A POOR PROGNOSIS FACTOR, AND A THERAPEUTIC TARGET IN MULTIPLE CANCER TYPES

This application claims the benefit of U.S. Provisional Application No. 60/501,786, filed on Sep. 10, 2003, which is incorporated by reference in its entirety.

The government owns rights in the present invention pursuant to grant number USAMRMC DAMD-17-01-0306 from the U.S. Army.

BACKGROUND OF THE INVENTION

1. Field of the Invention

The present invention relates generally to the fields of cancer biology and molecular biology. More particularly, it concerns methods of determining prognosis in a subject with a hyperproliferative disease that involve determining expression and/or function of 14-3-3 zeta in the subject. It also concerns methods of making a pharmaceutical agent that modulates apoptosis, including the steps of obtaining one or more candidate, testing the one or more candidate substances to determine their ability to modulate the expression and/or function of 14-3-3 zeta, selecting a candidate substance determined to modulate the expression and/or function of 14-3-3 zeta, and making a pharmaceutical composition that includes the selected candidate substance. In addition, the present invention concerns methods of treating a subject with a hyperproliferative disease, including making a pharmaceutical agent by any of the methods set forth herein, and administering the pharmaceutical agent to a subject.

2. Description of Related Art

The 14-3-3 proteins constitute a family of highly conserved dimeric proteins that are ubiquitously expressed in eukaryotic organisms (Aitken et al., 1992). These proteins were originally isolated in 1967 (Moore and Perez, 1967). The name "14-3-3" is derived from the particular migration pattern on two-dimensional DEAE-cellulose chromatography and starch gel electrophoresis (Moore and Perez, 1967). In humans, nine isoforms have been found to be encoded by seven 14-3-3 genes. The encoded proteins have a molecular weight of 29 kDa -31 kDa.

High levels of 14-3-3 proteins were originally shown to exist in neuronal tissue, and it was originally thought that they were neuron-specific (Moore and Perez, 1967). However, they have now been shown to be widely distributed and present at low levels in most mammalian tissues. Proteins that show a high degree of similarity have been cloned and sequenced from a wide range of other eukaryotic organisms including plants, insects, amphibians and yeast (Aitken et al., 1992).

The 14-3-3 family is highly conserved over a wide range of mammalian species, and the 14-3-3 isoforms can be found in an extremely broad range of tissues. There are very high levels of many isoforms in brain tissue, particular Purkinje cells in the cerebellum (Watanabe et al., 1991). High levels of beta and gamma isoforms are also found, the latter of which is believed to be specific for the brain (Isobe et al., 1991). There are also high levels of some isoforms in adrenal medulla and intestine, platelets, and testis (Ichimura et al., 1991). Other isoforms are expressed in spleen, skin, ear, and tongue (Aitken et al., 1992). Homologues of 14-3-3 proteins have been found in a broad range of eukaryotic organisms and are probably ubiquitous (reviewed in Wang and Shakes, 1996; Rosenquist et al., 2000).

Crystal structures of both the tau and zeta isoforms of 14-3-3 show that they are highly helical, dimeric proteins (Xiao et al., 1995; Liu et al., 1995). Each monomer is composed of nine anti-parallel α-helices, organized into an N-terminal and a C-terminal domain. The dimer creates a large negatively charged channel. Those regions of the 14-3-3 proteins which are invariant throughout all of the isoforms are mainly found lining the interior of this channel, while the variable residues are located on the surface of the protein (Aitken et al., 2002). This channel might recognize common features of target proteins, so the specificity of interaction of 14-3-3 isoforms with diverse target proteins may involve the outer surface of the protein (Aitken et al., 2002). The N-terminal residues of all 14-3-3 homologues are variable, and are involved in dimer formation (Aitken et al., 2002).

The known functions of the 14-3-3 class of proteins include a wide range of cell signaling processes as well as development and growth regulation. The first function of this family of proteins that was described was activation of tyrosine and tryptophan hydroxylases, the rate-limiting enzymes involved in catecholamine and serotonin biosynthesis, essential for the synthesis of dopamine and other neurotransmitters (Ichimura et al., 1988). Subsequently, it was shown that 14-3-3 could regulate (inhibit) activity of protein kinase C (PKC) (Aitken et al., 1990; Toker et al., 1990). 14-3-3 was then found to be a novel type of chaperone protein that modulates the interaction between components of signal-transduction pathways (Aitken, 1996). Previous studies indicated that different 14-3-3 isoforms have overlapping roles within cells as they bind many of the same target proteins (Yaffe, 2002).

In the mid-1990's, numerous reports showed that 14-3-3 proteins could interact with a wide range of protein kinases, phosphatases, and other signaling proteins (reviewed in Aitken et al., 2002), which implies that 14-3-3 proteins mediate the formation of protein complexes involved in signal transduction, trafficking and secretion, perhaps to bind to different signaling proteins on each subunit of the dimer, as a novel type of 'adapter protein.'

In addition, 14-3-3 proteins play a role in suppression of apoptosis. They bind many proteins involved in regulation of apoptosis, such as BAD (Zha et al., 1996), A20 (De Valck et al., 1997), Forkhead (Brunet et al., 1999), and ASK1 (Zhang et al., 1999). Compromising 14-3-3 function by overexpression of a competitive 14-3-3 binding peptide rendered cells more sensitive to apoptotic stimuli (Masters and Fu, 2001).

One of the kinases that has been shown by the inventors to interact with 14-3-3 proteins is phosphatidylinositol 3-kinase (PI-3-kinase). The PI-3 kinases represent a ubiquitous family of heterodimeric lipid kinases that are found in association with the cytoplasmic domain of hormone and growth factor receptors and oncogene products. PI3Ks act as downstream effectors of these receptors, are recruited upon receptor stimulation and mediate the activation of second messenger signaling pathways through the production of phosphorylated derivatives of inositol (Fry et al., 1994). PI3Ks have also been implicated in many cellular activities including growth factor mediated cell transformation, mitogenesis, protein trafficking, cell survival and proliferation, DNA synthesis, apoptosis, neurite outgrowth and insulin-stimulated glucose transport reviewed in (Fry et al.,1994).

The PI3-kinase enzyme heterodimers most commonly consist of a 110 kD (p 110) catalytic subunit associated with an 85 kD (p85) regulatory subunit. Recently however, three smaller regulatory subunits have been identified, two 55 kD subunits (p55.alpha. and p55.gamma.) and one 50 kD subunit (p50.alpha.) (Shin et al., 1998). Modulation of PI3-kinase activity by 14-3-3 zeta in cancer cells is not established from previous studies. (Munday et al., 2000; Guthridge et al., 2000; Liu et al., 1996). These previous studies concerned hematopoietic rather than cancer cells.

Cancer is a major cause of morbidity and mortality in the si U.S. Breast cancer, for instance, now affects as many as one in eight women during their lifetime (Ries et al., 1999; Sondik 1994). In many regions of the world, breast cancer is the more frequently occurring malignant disease in women (Forbes, 1997). Methods of diagnosing and treating breast cancer are a major research focus in the U.S.

Although many biomarkers for breast cancers (e.g., estrogen receptor, ErbB2, Bcl-2) have been discovered during the last decades, ideal prognostic factors for breast cancers are still lacking (Rogers et al., 2002). For instance, only about 30% of breast cancers overexpress c-erb2, epidermal growth factor receptor, cyclin D1, or c-myc (reviewed in Welch and Wei, 1998).

There is no clear role of 14-3-3 isoforms in human cancer. In particular, there has been no previous report on tumor promoting function of 14-3-3 isoforms in human cancers. Recently, however, loss of 14-3-3 sigma gene expression was found to be a frequent event in breast cancer (Ferguson et al., 2000). The 14-3-3 sigma isoform is believed to be responsible for instituting the $G_2$ cell cycle checkpoint response to DNA damage in human cells (Hermeking et al., 1997; Chan et al., 2000). Although 14-3-3 sigma has been associated with tumor suppression (Ferguson et al., 2000), this function has not been ascribed to other 14-3-3 isoforms. Another study found that levels of the alpha, beta, delta, and zeta isoforms of 14-3-3 were the same in both normal and transformed cells (Vercoutter-Edouart et al., 2001). These results indicate that the precise role of the 14-3-3 family of proteins in human cancer remains ill-defined.

Therefore, the identification of the precise role of 14-3-3 proteins in human cancer may provide valuable insight that can be applied in the clinical care of cancer patients. Detailed elucidation of any relationship between 14-3-3 expression and cancer could provide new forms of cancer therapy. Knowledge of a correlation between 14-3-3 protein levels and cancer severity or cancer type could be applied in formulating accurate prognosis of cancer patients, and could also be applied in designing targeted therapeutic and preventive strategies.

SUMMARY OF THE INVENTION

The inventors have discovered that 14-3-3 zeta expression is elevated in many types of human cancers, including breast cancer, sarcomas, lung cancer, liver cancer, uterine cancer, and stomach cancer. It has further been determined that 14-3-3 zeta is overexpressed in over 70% of human breast cancers, soft tissue sarcomas, and in many breast cancer cell lines, lung cancer cell lines, and soft tissue sarcoma cell lines. The inventors found that patients with 14-3-3 zeta-overexpressing breast cancers had significantly lower disease-free and overall survival rates. These findings demonstrate that overexpression of 14-3-3 zeta is a frequent event in multiple types of cancers, is associated with poor prognosis, and can be used as a novel molecular marker to assess the agressiveness of a variety of cancer types and the need for more vigorous therapies. In addition, 14-3-3 zeta is a novel clinical therapeutic target in multiple cancer types, and blocking 14-3-3 zeta expression and/or function is an effective strategy to inhibit multiple types of cancers.

Certain embodiments of the present invention generally pertain to methods of determining prognosis in a subject with a hyperproliferative disease. Determining prognosis involves a prediction of the probable course and outcome of a disease, or the likelihood of recovery from a disease. These methods of determining prognosis involve determining expression and/or function of 14-3-3 zeta in a subject. Any method of determining expression and/or function of 14-3-3 zeta in a subject that is known to those of ordinary skill in the art is encompassed within the embodiments of the invention.

In some embodiments, expression and/or function of 14-3-3 zeta is measured in a body fluid sample or tissue sample from the subject. Any body fluid sample from a subject is contemplated by the embodiments of the present invention. For example, in certain embodiments, the body fluid sample is a serum sample, a plasma sample, a blood sample, a cerebrospinal fluid sample, a urine sample, or a sample of fluid aspirated from a hyperproliferative lesion such as a breast lesion. Similarly, any tissue sample from a subject is contemplated by the embodiments of the present invention. In certain embodiments, for example, the tissue sample may be tissue from a hyperproliferative lesion in a subject. The hyperproliferative lesion may be a cancer, such as breast cancer, lung cancer, ovarian cancer, brain cancer, liver cancer, cervical cancer, colon cancer, renal cancer, skin cancer, head & neck cancer, bone cancer, esophageal cancer, bladder cancer, uterine cancer, lymphatic cancer, stomach cancer, pancreatic cancer, testicular cancer, lymphoma, or leukemia.

In some specific embodiments of the present invention, expression and/or function of 14-3-3 zeta is measured in a cell in a subject. Any cell in a subject is contemplated by the present invention. For example, the cell may be a cell from a hyperproliferative lesion, such as a cancer of any of the types previously set forth. In certain particular embodiments, the cell is a breast cancer cell.

Any subject is contemplated for inclusion in the embodiments of the present invention. In certain specific embodiments, for example, the subject is a human. The human may be afflicted by a hyperproliferative disease, such as a cancer. For example, as set forth above, the cancer may be breast cancer, lung cancer, ovarian cancer, brain cancer, liver cancer, cervical cancer, colon cancer, renal cancer, skin cancer, head & neck cancer, bone cancer, esophageal cancer, bladder cancer, uterine cancer, lymphatic cancer, stomach cancer, pancreatic cancer, testicular cancer, lymphoma, or leukemia. In some embodiments, the patient is a breast cancer patient.

Any method of determining expression and/or function of 14-3-3 zeta known to those of ordinary skill in the art is contemplated for inclusion in the embodiments of the present invention. For example, determining expression and/or function of 14-3-3 zeta may be measured by western blot analysis, immunohistochemistry, and/or protein array. In some embodiments, expression and/or function of 14-3-3 is measured by determining mRNA transcription as an indirect measure of 14-3-3 zeta protein expression in a cell. In other embodiments, measuring 14-3-3 zeta expression is determined by measuring gene copy number of 14-3-3 zeta as an indirect measure of 14-3-3 zeta protein expression in a cell. Gene copy number may be measured by any method known to those of ordinary skill in the art, such as FISH, array CGH, Southern blot analysis, and/or quantitative real time PCR.

Certain other embodiments of the present invention are generally concerned with methods of making a pharmaceutical agent that modulates apoptosis, including the steps of: (1) obtaining one or more candidate substances; (2) testing the one or more candidate substances to determine their ability to modulate the expression and/or function of 14-3-3 zeta; (3) selecting a candidate substance determined to modulate the expression and/or function of 14-3-3 zeta; and (4) making a pharmaceutical composition comprising the selected candidate substance. Any candidate substance is contemplated by the present invention. For example, the candidate substance may be a small molecule, a peptide, a polypeptide, a protein, a polynucleotide, antibody, or an si RNA. In some embodiments, the candidate substance is si RNA.

In some embodiments, the methods of the present invention further include administering the pharmaceutical agent to a subject having a hyperproliferative disease. The hyperproliferative disease may be a cancer, such as a cancer of any of the types set forth above. In some embodiments, the cancer is breast cancer.

In some embodiments, the present invention includes contacting the candidate substance with a cell and measuring expression and/or function of 14-3-3 zeta in the cell. Any cell is contemplated for inclusion in the present invention. For example, the cell may be a cell in a subject, such as a human. The human may be a patient with cancer, such as a patient with breast cancer.

Any method of testing the one or more candidate substances to determine their ability to modulate the expression and/or function of 14-3-3 zeta known to those of ordinary skill in the art is contemplated for inclusion in the present invention. For example, testing the one or more candidate substances to determine their ability to modulate the expression and/or function of 14-3-3 zeta may further be defined as testing the one or more candidate substances to determine their ability to modulate the interaction of 14-3-3 zeta with PI-3-kinase. Ability to modulate any mechanism of interaction of 14-3-3 zeta with PI-3-kinase is contemplated by the methods of the present invention. For example, testing of the interaction of 14-3-3 zeta with the p85 subunit of PI3-kinase is contemplated, as is testing of the interaction of 14-3-3 zeta with serine 83 of the p85 subunit of PI-3-kinase.

Some embodiments of the present invention pertain to methods of treating a subject with a hyperproliferative disease that involve making a pharmaceutical agent by any of the methods set forth above, and administering the pharmaceutical agent to a subject. Although any subject is contemplated for inclusion in the methods of the present invention, in some embodiments the subject is a patient with cancer. The subject may have any type of cancer. Some examples of cancer types have been set forth above. For example, in certain embodiments, the cancer is breast cancer.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A: Colony formation in soft agar of 435.neo (■) and 435.1433 zeta (□) cells in indicated serum concentrations. Colonies were counted and the fold increase in colony numbers determined. The data show that increased 14-3-3 zeta expression in 435.1433 zeta cells leads to increased colony formation. FIG. 1B: 435.neo (■) and 435.1433 zeta (□) cells were exposed to γ-radiation, and apoptosis was assayed by FACS analyses of annexin-positive cells at 0 hour and after 72 hours. The data show that higher 14-3-3 zeta expression in 435.1433 zeta cells confers resistance to IR-induced apoptosis. FIG. 1C: MDA-MB-435 cells were transfected by mock (◇), control (□), or 14-3-3 zeta (■) siRNA. Cells were plated in 24-well plates in either 10% or 0.5% serum and counted on the indicated days to determine the growth rate. FIG. 1D: The indicated cell lines were treated with control (□) or 14-3-3 zeta (■) siRNAs. The cells were collected 72 hours post-transfection and cell cycle $G_1$ percentage were determined by FACS analysis. These data show that downregulation of 14-3-3 zeta by siRNA leads to reduced cell proliferation by inducing a $G_1$ arrest.

FIG. 2A: MCF-7 cells were treated with 14-3-3 zeta (■), or control (□) siRNAs. Forty-eight hours post-transfection, the cells were split into multiple plates, allowed to attach for 24 hours, and replenished with serum-free media. At the indicated time points, apoptotic cells were identified by annexin-V staining and FACS analysis. FIG. 2B: MCF-7 breast cancer cells and HeLa cervical cancer cells were treated as discussed in Example 1 and propidium iodide staining and FACS analysis identified the sub-G1 phase. FIG. 2C: MCF-7 cells were treated as in FIG. 2A except a duplicate well of cells were also treated with Z-VAD-FMK caspase inhibitor for 24 hours in serum-free media. The annexin-positive cells were analyzed as in FIG. 2A. FIG. 2D: MCF-7 and MDA-MB-435 cells were transfected with 14-3-3 zeta (■) or control (□) siRNAs. Colony formation in 10% FBS soft agar was determined by crystal violet staining on day 14. FIG. 2E and FIG. 2F: MDA-MB-435 cells were treated with mock (◇), control (□) or 14-3-3 zeta (■) siRNA, and $1 \times 10^6$ cells were injected into the mammary fat pads of SCID mice (10 mice/group). In FIG. 2E, tumor onset was determined by measurable tumors on the indicated days. In FIG. 2F, the tumor volume was determined by measuring the length and width of the tumors on the indicated days.

FIG. 4A: MCF-7 and H1299 cells were stably transfected with HA-14-3-3 zeta expression vector. Cells were either grown in 10% FBS/DMEM media (+), serum starved for 18 hours (−), or serum starved for 18 hours then stimulated with 10% FBS/DMEM media for 10 or 30 minutes (10', 30'), lysed and immunoprecipitated with HA antibody to bring down 14-3-3 zeta and 14-3-3 zeta binding proteins. Interaction of HA-14-3-3 zeta and endogenous p85 was analyzed by western blotting using anti-p85. Immunoprecipitation with IgG was included as a negative control. FIG. 4B: MCF-7 cells stably transfected with HA-14-3-3 zeta were treated as in FIG. 4A. −/+ indicates cells were serum starved for 18 hr and then stimulated for 10 minutes. Cell lysates were immunoprecipitated with antibodies to p85, p110 or IgG as control. Interactions of endogenous p85 and p110 with HA-14-3-3 zeta were analyzed by western blotting using anti-HA to detect bound 14-3-3 zeta. These data indicates 14-3-3 zeta can associate with both subunits of PI3K. FIG. 4C: MCF-7 cells were treated with siRNA to 14-3-3 zeta or a control. Cells were serum starved for 18 hours then stimulated with Heregulin for 10 minutes (−/+ HRG), lysed and immunoprecipitated with a general phospho-tyrosine antibody (PY20) to pull down activated receptor tyrosine kinases and associated proteins. Immunoprecipitates were subjected to PI-3K assays. Kinase activity was determined by production of PIP3. The data show downregulation of 14-3-3 zeta reduces PI3K activity when stimulated with Heregulin. FIG. 4D: MCF-7 and MDA-MB-435 cells were treated with siRNA to 14-3-3 zeta or a control. Forty-eight hours post-transfection, the cells were split into multiple plates, allowed to attach for 24 hours and replenished with serum-free media for 18 hours. Cells were re-stimulated with 10% FBS/DMEM media and collected at the indicated time points (minutes). Akt activity was determined by measuring Akt phosphorylation status using western blot analysis with a phospho-serine 473 Akt antibody. Immunoblot of Akt was used as a loading control. The data indicate 14-3-3 zeta is important for Akt activation by serum.

FIG. 5A: MCF-7 cells were stably transfected with HA-14-3-3 zeta and histidine tagged (HIS) wild type p85 ($p85^{wt}$) or p85 with serine 83 mutated to alanine ($p85^{S83A}$) or an empty vector. Expression levels were determined by western blot analysis using p85 antibody (upper panel) and HA antibody (lower panel). FIG. 5B: Stably transfected MCF-7 cells in FIG. 5A were serum starved for 18 hours and stimulated with 10% FBS/DMEM media, lysed, and immunoprecipitated with p85 antibody or HIS antibody to bring down total p85 or HIS-tagged p85. Association of HA-14-3-3 zeta with the indicated p85 proteins was determined by western blot analysis using HA antibody (lower panel) and IP efficiency was determined by western blot with p85 antibody. The data indicate that serine 83 is important for 14-3-3 zeta association with p85. FIG. 5C: MCF-7 cells stably transfected as in FIG. 5A were grown in 10% FBS/DMEM media, lysed and immunoprecipitated with a phospho-tyrosine antibody (PY20) to pull down activated receptor tyrosine kinases and associated proteins. Immunoprecipitates were subjected to PI3K assays (left panel). PI3K activity was determined by production of PIP3. The graph represents relative percent PI3K activity for the indicated p85 proteins (right panel). Data shown is a quantitative analysis of PI-3K activity determined by dividing the intensity of the PIP3 signal by the intensity of the PIP3 and origin signals. FIG. 5D: MCF-7 cells in FIG. 5A were maintained in 10% FBS/DMEM media. Akt activity was measured by western blot analysis using phospho-serine 473 Akt antibody. Immunoblot of Akt was used as loading control. Relative intensity of phospho-Akt was calculated by dividing the band intensity of phospho-Akt by Akt. The vector phospho-Akt/Akt ratio was set as in FIG. 4. FIG. 5E: MCF-7 cells in FIG. 5A were serum starved for the indicated time periods. Apoptotic cells were identified by TUNEL and FACS analysis. The data indicate that 14-3-3 zeta association with p85 is necessary for complete activation of PI-3K and Akt and disruption of 14-3-3 zeta association with p85 sensitizes cells to apoptosis induced by serum starvation.

DESCRIPTION OF ILLUSTRATIVE EMBODIMENTS

Figure 1:
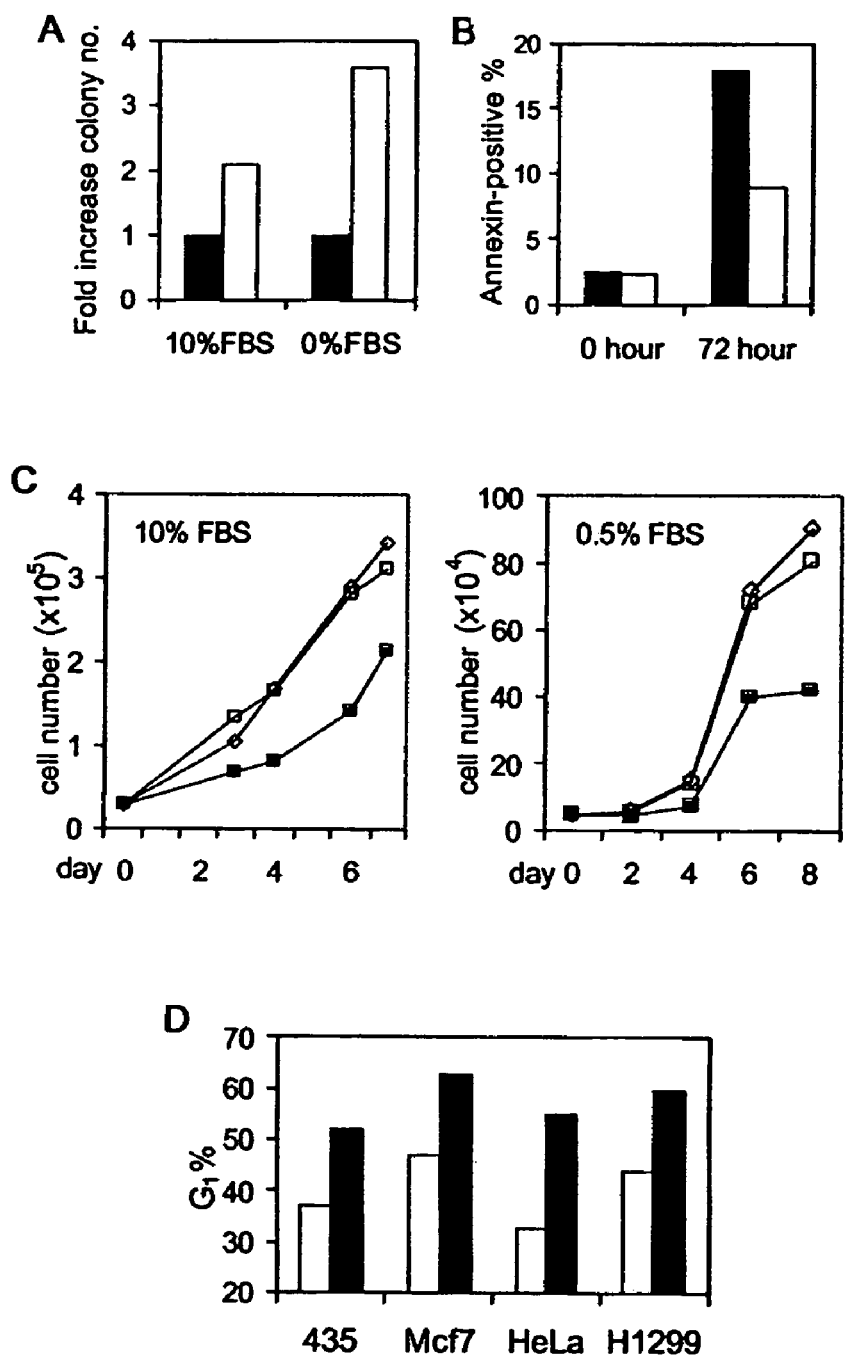
FIG. 1A, FIG. 1B, FIG. 1C, FIG. 1D. Specific silencing of 14-3-3 zeta reduces cell proliferation by inducing a $G_1$ arrest.

The present invention seeks to exploit the inventors' discovery by providing for methods of determining prognosis in a subject with a hyperproliferative disease, such as cancer, that involve determining 14-3-3 zeta expression and/or function in a subject. For example, increased 14-3-3 zeta expression in a biopsy sample from a tumor of a subject with cancer may be used to indicate poorer prognosis, and the need for a more aggressive therapeutic regimen.

The present invention also provides for methods of making a pharmaceutical agent that modulates apoptosis, involving the steps of: (1) obtaining one or more candidate substances; (2) testing the one or more candidate substances to determine their ability to modulate the expression and/or function of 14-3-3 zeta; (3) selecting a candidate substance determined to modulate the expression and/or function of 14-3-3 zeta; and (4) making a pharmaceutical composition that includes the selected candidate substance. The present invention also provides for methods of treating a subject with a hyperproliferative disease, including making a pharmaceutical agent by any of the methods set forth herein, and administering the pharmaceutical agent to the subject.

A. 14-3-3 Zeta Protein

Throughout this application, the term "14-3-3 zeta" is intended to refer to the exemplified 14-3-3 zeta molecules as well as all 14-3-3 zeta homologues from other species. The full-length amino acid sequence of the human 14-3-3 zeta protein is provided herein, and is designated SEQ ID NO:1 (GenBank Accession Number NP_003397).

The term "14-3-3 zeta" refers to both "wild-type" and "mutant" 14-3-3 zeta. Wild-type 14-3-3 zeta refers to a 14-3-3 zeta molecule having normal 14-3-3 zeta activity, as exemplified by SEQ ID NO:1. Mutant 14-3-3 zeta includes sequence variants of 14-3-3 zeta that may or may not have reduced 14-3-3 zeta activity.

Inherent in the definition of sequence variants is the concept that there is a limit to the number of amino acid changes that may be made within a defined portion of the molecule and still result in a molecule with an acceptable level of equivalent biological activity, i.e., ability of 14-3-3 zeta to modulate cell death. Sequence variants are thus defined herein as those polypeptides in which certain, not most or all, of the amino acids may be substituted. Of course, a plurality of distinct proteins/polypeptides/peptides with different substitutions may easily be made and used in accordance with the invention.

Amino acid sequence variants of the polypeptide can be substitutional mutants or insertional mutants. Insertional mutants typically involve the addition of material at a non-terminal point in the peptide. This may include the insertion of a few residues; an immunoreactive epitope; or simply a single residue. The added material may be modified, such as by methylation, acetylation, and the like. Alternatively, additional residues may be added to the N-terminal or C-terminal ends of the peptide.

Amino acid substitutions are generally based on the relative similarity of the amino acid side-chain substituents, or example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

Throughout this application, the terms "14-3-3 zeta activity," "14-3-3 zeta expression," and "14-3-3 zeta function" refer to the activity, expression, and function of the 14-3-3 zeta protein. As used herein in this application, 14-3-3 zeta protein includes 14-3-3 zeta proteins from any and all species, including the human protein. 14-3-3 zeta activity or 14-3-3 zeta function refers to the functional activity of the 14-3-3 zeta protein. Any method known to those of skill in the art can be used to quantitate functional activity of the 14-3-3 protein. For example, increased cell death can be used as a measure of decreased 14-3-3 zeta activity.

14-3-3 zeta expression refers to expression of the 14-3-3 protein. 14-3-3 zeta expression can be measured directly, such as by protein assays. For example, 14-3-3 zeta expression can be measured by western blot analysis, immunohistochemistry, protein array, or any method known to those of skill in the art. Alternatively, 14-3-3 expression can be measured indirectly, such as by measurement of 14-3-3 zeta mRNA transcription and/or stability, measurement of gene copy number of the 14-3-3 zeta gene in a cell, or any method known to those of skill in the art.

In certain embodiments, the 14-3-3 zeta protein may be purified. Generally, "purified" will refer to a 14-3-3 zeta protein composition that has been subjected to fractionation to remove various other proteins, polypeptides, or peptides, and which composition substantially retains its activity. Purification may be substantial, in which the 14-3-3 zeta is the predominant species, or to homogeneity, which purification level would permit accurate degradative sequencing.

The 14-3-3 zeta protein purified from a natural source or from recombinantly-produced material. Those of ordinary skill in the art would know how to produce these polypeptides from recombinantly-produced material. This material may use the 20 common amino acids in naturally synthesized proteins, or one or more modified or unusual amino acids.

Any method known to those of ordinary skill in the art can be used to purify the 14-3-3 zeta protein. Purification methods, for example, may result in 14-3-3 zeta protein that has been purified to at least about 20%, 25%, 30%, 35%, 40%, 45%, 50%, 55%, 60%, 65%, 70%, 75%, 80%, 85%, 90%, 95% and up to about 100% homogeneity. Alternatively, 14-3-3 zeta protein may be purified to at least or at most about 20%-95%, 30%-90%, 40%-80%, 50%-75%, 20%-50%, 50%-70%, 50%-90%, 70%-90% and ranges in between. The term "homogeneity" refers to the percent of 14-3-3 zeta protein as compared to the total amount of protein (by molecule). The term "about" refers to the imprecision of determining protein amounts, and is intended to include at least one standard deviation of error for any particular assay or calibration for measuring protein concentration. For example, if protein concentration and homogeneity is measured by gel electrophoresis with coomassie gel staining, 14-3-3 zeta protein that has been purified to at least about 25% homogeneity means that the sample placed on the gel is at least 25% 14-3-3 zeta, as compared to total protein concentration by molecule, plus or minus the standard deviation for a protein gel stained with coomassie dye.

B. Candidate Substances

The present invention includes methods of making a pharmaceutical agent that modulates apoptosis, including the steps of obtaining one or more candidate, testing the one or more candidate substances to determine their ability to modulate the expression and/or function of 14-3-3 zeta, selecting a candidate substance determined to modulate the expression and/or function of 14-3-3 zeta, and making a pharmaceutical composition that includes the selected candidate substance.

Apoptosis, or programmed cell death, is an essential process for normal embryonic development, maintaining homeostasis in adult tissues, and suppressing carcinogenesis (Kerr et al., 1972). Apoptosis refers to, for example, cell shrinkage, chromatin condensation, nucleus concentration, disappearance of microvillus on the cell surface, plasma membrane blebbing, apoptotic body formation, gap between peripheral cells accompanied with cell shrinkage, and removal by phagocytes (Japan Clinic, vol.54, No. 7 (1996)). Apoptosis or programmed cell death plays an important role in individual development and homeostasis maintenance in a living body. It has been gradually made clear that abnormality of apoptosis causes diseases such as cancers, autoimmune diseases and nervous diseases.

Any method of testing a candidate substance known to those of ordinary skill in the art is contemplated by the present invention. For example, assays to assess ability of the candidate substance to modulate expression and/or function of 14-3-3 zeta are contemplated. The assays may comprise random high-throughput screening of large libraries of candidate substances. Alternatively, the assays may be used to focus on particular classes of compounds selected with an eye towards structural attributes that are believed to make them more likely to modulate the function of this molecule. The assays may be cell-free assays, in vitro assays, in cyto assays, in vivo assays, or any assay technique known to those of skill in the art.

By function, it is meant that one may assay for effects on function of 14-3-3 zeta. For example, a candidate substance can be analyzed for its ability to bind to 14-3-3 zeta.

Alternatively, the candidate substance can be analyzed for its ability to interfere with the ability of 14-3-3 zeta to prevent cell death. For example, the cell can be analyzed for apoptosis and other histological changes associated with cell death.

A modulator of the expression and/or function of 14-3-3 zeta is any substance that can inhibit or promote the expression and/or function of 14-3-3 zeta.

The candidate substance can be a candidate substance suspected of either inhibiting or promoting apoptosis.

1. Modulators

As used herein the term "candidate substance" refers to any molecule that may potentially inhibit or enhance apoptotic cell death. The candidate substance may be a protein or fragment thereof, a small molecule, an antibody, or even a polynucleotide.

The candidate substance may also be small interfering RNA ("siRNA") molecules. siRNA's for mammalian systems are typically composed of double-stranded RNA with 19 to 28, preferable 19 to 23, nucleotide RNA strands, a two nucleotide overhand at the 3' end and an optional 5' phosphate group (Yang et al., 2001; Elbashir et al., 2002). Such siRNA's provide a highly active and selective method for reducing the expression of targeted genes by utilizing the RNA interference post-translational gene silencing pathway. Interference of gene expression by interfering RNA is recognized as a naturally occurring mechanism for silencing alleles during development in plants, invertebrates and vertebrates.

It may prove to be the case that the most useful pharmacological compounds will be compounds that are structurally related to 14-3-3 zeta protein, i.e., mimics. Using lead compounds to help develop improved compounds is known as "rational drug design" and includes not only comparisons with known inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single-chain antibodies or expression constructs coding thereof), each of which would be specific for a given target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

A modulator (i.e., inhibitor or activator) according to the present invention may be one which exerts its inhibitory or activating effect upstream, downstream or directly on the function of the 14-3-3 zeta protein. Regardless of the type of inhibitor or activator identified by the present screening methods, the effect of the inhibition or activator by such a compound results in an altered expression and/or function of 14-3-3 zeta compared to the absence of the added candidate substance.

2. In vitro Assays

A quick, inexpensive and easy assay to run is an in vitro assay. Such assays can be run quickly and in large numbers, thereby increasing the amount of information obtainable in a short period of time. A variety of vessels may be used to run the assays, including test tubes, plates, dishes and other surfaces such as dipsticks or beads. One example of a cell free assay is a binding assay. While not directly addressing function, the ability of a candidate substance to modulate 14-3-3 zeta expression and/or function is strong evidence of a related biological effect. For example, binding of a molecule to a target may, in and of itself, be inhibitory, due to steric, allosteric or charge-charge interactions. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564, U.S. Pat. No. 6,457,809, U.S. Pat. No. 6,406,921, and U.S. Pat. No. 5,994,131. Large numbers of small peptide test compounds are synthesized on a solid substrate, such as plastic or some other surface. Bound polypeptide is detected by various methods.

3. In cyto Assays

In certain embodiments of the present invention, the method of making a pharmaceutical agent that modulates apoptosis involves contacting the candidate substance with a cell. The cell can then be assayed for various parameters associated with modulation of 14-3-3 zeta activity. For instance, the cells can be directly assayed for binding inhibition of 14-3-3 zeta expression. Immunohistochemical techniques, confocal techniques, or other techniques to assess binding are well known to those of skill in the art.

Various cell lines can be utilized for such screening assays, including cells specifically engineered for this purpose. Examples of cells used in the screening assays include cancer cells, cells infected with a virus, foam cells, macrophages, neuronal cells or dendritic cells. The cell may be a stimulated cell, such as a cell stimulated with a growth factor. One of skill in the art would understand that the invention disclosed herein contemplates a wide variety of in cyto assays for measuring parameters that correlate with modulation of 14-3-3 zeta activity.

Depending on the assay, culture may be required. The cell may be examined using any of a number of different physiologic assays to assess for modulation of 14-3-3 zeta activity. Alternatively, molecular analysis may be performed, for example, looking at protein expression, mRNA expression (including differential display of whole cell or polyA RNA) and others such as measurement of 14-3-3 gene copy number.

4. In vivo Assays

In vivo assays involve the use of various animal models, including transgenic animals that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate substances are administered to an animal, and the ability of the candidate substance(s) to alter one or more characteristics, as compared to a similar animal not treated with the candidate substance(s), identifies a modulator. The characteristics may be any of those discussed above with regard to the functions associated with 14-3-3 zeta (e.g., cell survival).

The present invention provides methods of screening of a candidate substance that can modulate death of a cancer cell. Treatment of these animals with test compounds will involve the administration of the compound, in an appropriate form, to the animal. Any animal model of cancer known to those of skill in the art can be used in the screening techniques of the present invention. Administration will be by any route that could be utilized for clinical or non-clinical purposes, including but not limited to oral, nasal, buccal, intratumoral, or even topical. Alternatively, administration may be by intratracheal instillation, bronchial instillation, intradermal, subcutaneous, intramuscular, intraperitoneal. inhalation or intravenous injection.

Determining the effectiveness of a compound in vivo may involve a variety of different criteria. Also, measuring toxicity and dose response can be performed in animals in a more meaningful fashion than in in vitro or in cyto assays.

C. Nucleic Acids, Vectors and Regulatory Signals

The present invention involves methods of making a pharmaceutical agent that modulates apoptosis, that involves testing one or more candidate substances to determine their ability to modulate expression and/or function of 14-3-3 zeta. In some embodiments of the present invention, the candidate substance is included in an expression cassette that includes a promoter, active in a particular cell, such as a cell in a subject, operably linked to a polynucleotide encoding the modulator.

Throughout this application, the term "expression cassette" is meant to include any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of a mRNA into a polypeptide.

As used in this application, the term "polynucleotide" refers to a nucleic acid molecule, RNA or DNA, that has been isolated free of total genomic nucleic acid. Therefore, a "polynucleotide encoding a modulator of 14-3-3 zeta" refers to a nucleic acid segment that contains a sequence that encodes a modulator of 14-3-3 zeta activity, yet is isolated away from, or purified and free of, total genomic DNA and proteins.

The present invention also encompasses derivatives of 14-3-3 zeta that have certain amino acid changes in comparison to 14-3-3 zeta protein. The mRNA sequence encoding the full-length amino acid sequence of human 14-3-3 zeta is provided below as SEQ ID NO:2 (GenBank Accession Number NM_003406).

The term "gene" is used for simplicity to refer to a functional protein, polypeptide, or peptide-encoding unit. As will be understood by those in the art, this functional term includes genomic sequences, cDNA sequences, and smaller engineered gene segments that express, or may be adapted to express, proteins, polypeptides, domains, peptides, fusion proteins, and mutants. The nucleic acid molecule encoding a modulator of 14-3-3 zeta may comprise a contiguous nucleic acid sequence of the following lengths or at least the following lengths: 5, 10, 20, 30, 40, 50, 60, 70, 80, 90, 100, 120, 140, 160, 180, 200, 220, 240, 260, 280, 300, 325, 350, 375, 400, 450, 500, 550, 600, 650, 700, 750, 800, 850, 900, 950, 1000, 1100, 1200, 1300, 1400, 1500, 1600, 1700, 1800, 1900, 2000, 2500, 3000, 3500, 4000, 4500, 5000, 5500, 6000, 6500, 7000, 7500, 8000, 8500, 9000, 9500, 10000, 11000, 12000 or more nucleotides, nucleosides, or base pairs, or any number of sequences that are encompassed in between each of these specified numbers of sequences. Such sequences may be complementary to SEQ ID NO:2 (14-3-3 zeta-encoding sequence).

The candidate substances of the present invention may include isolated DNA segments and recombinant vectors incorporating DNA sequences that encode a modulator of 14-3-3 zeta. In certain embodiments, the DNA segment may substantially correspond to a portion of SEQ ID NO:2. Accordingly, sequences that have about 70%, about 75%, about about 80%, 85%, about 90%, or about 95%, and any range derivable therein, such as, for example, about 70% to about 80%, and more preferably about 81% and about 90%; or even more preferably, between about 91% and about 99%; of amino acids that are identical or functionally equivalent to the amino acids of SEQ ID NO:1 are contemplated by the present invention.

Vectors of the present invention are designed, primarily, to transform cells with a therapeutic gene encoding a modulator of 14-3-3 zeta in which the gene is under the control of regulated eukaryotic promoters (i.e., inducible, repressable, tissue specific).

The term "promoter" will be used here to refer to a group of transcriptional control modules that are clustered around the initiation site for RNA polymerase II. One of ordinary skill in the art would be familiar with use of promoters. Any promoter familiar to one of ordinary skill in the art is contemplated by the present invention.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins. One of ordinary skill in the art would be familiar with use of enhancers, and the types of enhancers that are available.

Promoters and enhancers have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way.

Another signal that may prove useful is a polyadenylation signal. Such signals may be obtained from the human growth hormone (hGH) gene, the bovine growth hormone (BGH) gene, or SV40. One of ordinary skill in the art would be familiar with use of polyadenylation signals.

The use of internal ribosome binding sites (IRES) elements are used to create multigene, or polycistronic, messages. IRES elements are able to bypass the ribosome scanning model of 5-methylatd cap-dependent translation and begin translation at internal sites (Pelletier and Sonenberg, 1988). One of ordinary skill in the art would be familiar with techniques involving use of IRES elements.

In any event, it will be understood that promoters are DNA elements which when positioned functionally upstream of a gene leads to the expression of that gene. Most transgene constructs of the present invention are functionally positioned downstream of a promoter element.

D. Gene Transfer

1. Viral Vectors

Certain embodiments of the present invention pertain to methods of making a pharmaceutical agent that modulates apoptosis and methods of treating a subject using one of the pharmaceutical agents of the present invention. In certain embodiments, the selected candidate substance that is identified in the claimed methods of making a pharmaceutical agent is an expression cassette carried in a viral vector that is capable of modulating the expression and/or function of 14-3-3 zeta. A "viral vector" is meant to include those constructs containing viral sequences sufficient to (a) support packaging of the expression cassette and (b) to ultimately express a recombinant gene construct that has been cloned therein.

a. Adenoviral Vectors

One method for delivery of the recombinant DNA involves the use of an adenovirus expression vector.

Although adenovirus vectors are known to have a low capacity for integration into genomic DNA, this feature is counterbalanced by the high efficiency of gene transfer afforded by these vectors.

Adenoviruses are currently the most commonly used vector for gene transfer in clinical settings. Among the advantages of these viruses is that they are efficient at gene delivery to both nondividing an dividing cells and can be produced in large quantities. In many of the clinical trials for cancer, local intratumor injections have been used to introduce the vectors into sites of disease because current vectors do not have a mechanism for preferential delivery to tumor.

The vector comprises a genetically engineered form of adenovirus. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP (located at 16.8 m.u.), is particularly efficient during the late phase of infection, and all the mRNA's issued from this promoter possess a 5'-tripartite leader (TPL) sequence which makes them preferred mRNA's for translation.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1992).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

The adenovirus vector may be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

Adenovirus growth and manipulation is known to those of skill in the art, and exhibits broad host range in vitro and in vivo. This group of viruses can be obtained in high titers, e.g., $10^9$-$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

b. Retroviral Vectors

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990). One of ordinary skill in the art would be familiar with construction and use of retroviral vectors.

C. AAV Vectors

Adeno-associated virus (AAV) is an attractive vector system for use in the present invention as it has a high frequency of integration and it can infect nondividing cells, thus making it useful for delivery of genes into mammalian cells in tissue culture (Muzyczka, 1992). AAV has a broad host range for infectivity (Tratschin, et al., 1984; Laughlin, et al., 1986; Lebkowski, et al., 1988; McLaughlin, et al., 1988), which means it is applicable for use with the present invention. Details concerning the generation and use of rAAV vectors are described in U.S. Pat. No. 5,139,941 and U.S. Pat. No. 4,797,368, each incorporated herein by reference. One of ordinary skill in the art would be familiar with generation and use of AAV vectors.

d. Other Viral Vectors

Other viral vectors are familiar to those of ordinary skill in the art, and may be employed as constructs in the present invention. Examples include herpesvirus vectors and vaccinia virus vectors. Vectors derived from viruses such as poxvirus may be employed. A molecularly cloned strain of Venezuelan equine encephalitis (VEE) virus has been genetically refined as a replication competent vaccine vector for the expression of heterologous viral proteins (Davis et al., 1996). Studies have demonstrated that VEE infection stimulates potent CTL responses and has been suggested that VEE may be an extremely useful vector for immunizations (Caley et al., 1997). It is contemplated in the present invention, that VEE virus may be useful in targeting dendritic cells. In other embodiments of the present invention, lentiviral vectors or pox viral vectors are used. One of ordinary skill in the art would be familiar with the wide range of viral vectors that are available for use in the claimed invention.

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

e. Gene Delivery Using Modified Viruses

A polynucleotide may be housed within a viral vector that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

2. Nonviral Vectors a. Examples of Non-Viral Vectors

Several non-viral methods for the transfer of expression vectors into cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and liofectamine-DNA complexe, cell sonication (Fechheimer et al., 1987), gene bombardment using high velocity microprojectiles (Yang et al., 1990), polycations (Boussif et al., 1995) and receptor-mediated transfection (Wu and Wu, 1987; Wu and Wu, 1988). Some of these techniques may be successfully adapted for in vivo or ex vivo use. One of ordinary skill in the art would be familiar with the use of nonviral vectors, and techniques involving non-viral vectors.

E. Methods of Measuring Protein Expression

The present invention concerns methods of measuring prognosis in a subject with a hyperproliferative disease that include obtaining a cell or a body fluid sample from the subject and measuring increased expression and/or function of 14-3-3 zeta in the cell. Any method known to those of skill in the art can be used to measure increased expression and/or function of 14-3-3 zeta in the cell. A wide variety of techniques to measure protein expression in a cell or in a body fluid sample are known and familiar to one of ordinary skill in the art. Examples of these techniques include, but are not limited to, western blot analysis, immunohistochemistry staining, ELISA, and protein detection chips (tumor marker array).

1. Western Blot Analysis

Western blot analysis is an established technique that is commonly employed for analyzing and identifying proteins. The proteins are first separated by electrophoresis in polyacrylamide gel, then transferred ("blotted") onto a nitrocellulose membrane or treated paper, where they bind in the same pattern as they formed in the gel. The antigen is overlaid first with antibody, then with anti-immunoglobulin or protein A labeled with a radioisotope, fluorescent dye, or enzyme. One of ordinary skill in the art would be familiar with this commonly used technique for quantifying protein in a sample.

2. ELISAs

Immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used. One of ordinary skill in the art would be familiar with use of ELISAs and other immunohistochemical assays.

3. Immunohistochemistry

Techniques using antibodies be used in conjunction with both fresh-frozen and/or formalin-fixed, paraffin-embedded tissue blocks, such as blocks prepared from a tumor biopsy, prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1999; Allred et al., 1990). One of ordinary skill in the art would be familiar with immunohistochemistry as a means to study protein expression and/or function.

4. Protein Array Technology

Protein array technology allows high-throughput screening for gene expression and molecular interactions. Protein array technology is discussed in detail in Pandey and Mann (2000) and MacBeath and Schreiber (2000), each of which is herein specifically incorporated by reference. Protein arrays appear as new and versatile tools in functional genomics, enabling the translation of gene expression patterns of normal and diseased tissues into protein product catalog. Protein function, such as enzyme activity, antibody specificity, and other ligand-receptor interactions and binding of nucleic acids or small molecules can be analyzed on a whole-genome level.

a. Protein Biochip Assays

These arrays, which contain thousands of different proteins or antibodies spotted onto glass slides or immobilized in tiny wells, allow one to examine the biochemical activities and binding profiles of a large number of proteins at once. To examine protein interactions with such an array, a labeled protein is incubated with each of the target proteins immobilized on the slide, and then one determines which of the many proteins the labeled molecule binds.

The basic construction of protein chips has some similarities to DNA chips, such as the use of a glass or plastic surface dotted with an array of molecules. These molecules can be DNA or antibodies that are designed to capture proteins. Defined quantities of proteins are immobilized on each spot, while retaining some activity of the protein. With fluorescent markers or other methods of detection revealing the spots that have captured these proteins, protein microarrays are being used as powerful tools in high-throughput proteomics and drug discovery.

Glass slides are still widely used, since they are inexpensive and compatible with standard microarrayer and detection equipment. However, their limitations include multiple-based reactions, high evaporation rates, and possible cross-contamination. Matrix slides offer a number of advantages, such as reduced evaporation and no possibility of cross-contamination, but they are expensive. Nanochips for proteomics have the same advantages, in addition to reduced cost and the capability of multiple-component reactions.

The earliest and best-known protein chip is the ProteinChip by Ciphergen Biosystems Inc. (Fremont, Calif.). The ProteinChip is based on the surface-enhanced laser desorption and ionization (SELDI) process. Known proteins are analyzed using functional assays that are on the chip. For example, chip surfaces can contain enzymes, receptor proteins, or antibodies that enable researchers to conduct protein-protein interaction studies, ligand binding studies, or immunoassays. With state-of-the-art ion optic and laser optic technologies, the ProteinChip system detects proteins ranging from small peptides of less than 1000 Da up to proteins of 300 kDa and calculates the mass based on time-of-flight (TOF).

The ProteinChip biomarker system is the first protein biochip-based system that enables biomarker pattern recognition analysis to be done. This system allows researchers to address important clinical questions by investigating the proteome from a range of crude clinical samples (i.e., laser capture microdissected cells, biopsies, tissue, urine, and serum). The system also utilizes biomarker pattern software that automates pattern recognition-based statistical analysis methods to correlate protein expression patterns from clinical samples with disease phenotypes.

Some systems can perform biomarker discovery in days and validation of large sample sets within weeks. Its robotics system accessory automates sample processing, allowing hundreds of samples to be run per week and enabling a sufficient number of samples to be run, which provides high statistical confidence in comprehensive studies for marker discovery and validation.

b. Microfluidic Chip-Based Immunoassays

Microfluidics is one of the most important innovations in biochip technology. Since microfluidic chips can be combined with mass spectrometric analysis, a microfluidic device has been devised in which an electrospray interface to a mass spectrometer is integrated with a capillary electrophoresis channel, an injector, and a protein digestion bed on a monolithic substrate (Wang et al., 2000). This chip thus provides a convenient platform for automated sample processing in proteomics applications.

These chips can also analyze expression levels of serum proteins with detection limits comparable to commercial enzyme-linked immunosorbent assays, with the advantage that the required volume sample is markedly lower compared with conventional technologies.

c. Tissue Microarray Technology

Tissue microarray technology provides a high-throughput approach for linking genes and gene products with normal and disease tissues at the cellular level in a parallel fashion.

Compared with classical in situ technologies in molecular pathology that are very time-consuming, tissue microarrays provide increased throughput in two ways: up to 1000 tissue specimens can be analyzed in a single experiment, either at the DNA, RNA, or protein level; and tens of thousands of replicate tissue microarrays can be generated from a set of tissues. This process provides a template for analyzing many more biomarkers than has ever been possible previously in a clinical setting, even using archival, formalin-fixed specimens.

d. Nanoscale Protein Analysis

Most current protocols including protein purification and automated identification schemes yield low recoveries that limit the overall process in terms of sensitivity and speed. Such low protein yields and proteins that can only be isolated from limited source material (e.g., biopsies) can be subjected to nanoscale protein analysis: a nanocapture of specific proteins and complexes, and optimization of all subsequent sample-handling steps, leading to a mass analysis of peptide fragments. This focused approach, also termed targeted proteomics, involves examining subsets of the proteome (e.g., those proteins that are specifically modified, bind to a particular DNA sequence, or exist as members of higher-order complexes or any combination thereof). This approach is used to identify genetic determinants of cancer that alter cellular physiology and respond to agonists.

F. Methods of Indirectly Measuring Gene Expression

The present invention concerns methods of measuring prognosis in a subject with a hyperproliferative disease that include obtaining a cell or a body fluid sample from the subject and measuring increased expression and/or function of 14-3-3 zeta in the cell. Although expression and/or function of 14-3-3 zeta can be measured by one of the previously discussed assays, 14-3-3 zeta expression and/or function can be measured indirectly. For example, one can measure mRNA transcription in a cell or measurement of gene copy number in a cell.

1. Southern Blot Analysis

One of skill in the art would be familiar with the wide range of techniques for detecting levels of specific DNA fragments in a cell. One of the most well-known techniques is Southern blot analysis. Southern blot analysis is a technique for transferring DNA fragments separated by agarose gel electrophoresis to a nitrocellulose filter, on which specific fragments can then be detected by their hybridization to probes, which were labeled radioactively in the original technique but are now often labeled using nonradioactive methods.

2. Fluorescence In Situ Hybridization

Fluorescence in situ hybridization is a physical mapping approach that uses fluorescein tags to detect hybridization of probes with metaphase chromosomes and with the less-condensed somatic interphase chromatin. One of ordinary skill in the art would be familiar with this commonly used technique.

FISH methods can be used to detect microdelections that are not visible by standard cytogenetic banding patterns. FISH technology allows for the rapid determination of whether specific genes, loci, or regions are present or if deletions or amplifications have occurred. The sizes of these regions detected by FISH are usually much larger than detectable by PCR or Southern blot, yet much smaller than visualized microscopically by standard cytogenetics. This ability of FISH technology allows for its use in the diagnosis of cancer, prenatal, postnatal, and genetic diseases.

3. Measurement of mRNA

Gene expression may be determined by measuring the production of RNA. The RNA (e.g., mRNA) may be isolated and/or detected by methods well known in the art. Following detection, one may compare the results seen in a given cell line or individual (e.g., a tumor sample or a cell isolated from a body fluid sample) with a statistically significant reference group of control cells. Alternatively, one may compare production of RNA in cell lines transformed with the same gene operably linked to various mutants of a promoter sequence. In this way, it is possible to identify regulatory regions within a novel promoter sequence by their effect on the expression of an operably linked gene.

4. DNA Arrays and Gene Chip Technology

DNA arrays and gene chip technology provides a means of rapidly screening a large number of DNA samples for their ability to hybridize to a variety of single stranded DNA probes immobilized on a solid substrate. Specifically contemplated are chip-based DNA technologies such as those described by Hacia et al. (1996) and Shoemaker et al. (1996). These techniques involve quantitative methods for analyzing large numbers of genes rapidly and accurately. The technology capitalizes on the complementary binding properties of single stranded DNA to screen DNA samples by hybridization. Pease et al. (1994); Fodor et al. (1991). Basically, a DNA array or gene chip consists of a solid substrate upon which an array of single stranded DNA molecules have been attached. For screening, the chip or array is contacted with a single stranded DNA sample which is allowed to hybridize under stringent conditions. The chip or array is then scanned to determine which probes have hybridized. In a particular embodiment of the instant invention, a gene chip or DNA array would comprise probes specific for chromosomal changes evidencing the development of a neoplastic or preoplastic phenotype. In the context of this embodiment, such probes could include synthesized oligonucleotides, cDNA, genomic DNA, yeast artificial chromosomes (YACs), bacterial artificial chromosomes (BACs), chromosomal markers or other constructs a person of ordinary skill would recognize as adequate to demonstrate a genetic change.

A variety of gene chip or DNA array formats are described in the art, for example U.S. Pat. Nos. 5,861,242 and 5,578,832 which are expressly incorporated herein by reference. One of ordinary skill in the art would be familiar with the range of techniques available using DNA arrays.

5. Array CGH

The microarray-based form of comparative genomic hybridization (array CGH) detects and maps DNA sequence copy number variation throughout the entire genome onto a cytogenetic map supplied by metaphase chromosomes (Kallioniemi et al., 1992). The use of metaphase chromosomes as the hybridization target has previously limited the resolution of CGH to 10-20 Mb, prohibited resolution of closely speaced aberrations, and only allowed linkage of CGH results to genomic information and resources with cytogenetic accuracy. Array-based CGH, on the other hand, provides the capability to map copy number aberrations relative to the genome sequence, with the resolution being determined by the spacing of the clones. In array CGN, arrays of genomic VAC, P1, cosmid or cDNA clones are used as the hybridization target in place of the metaphase chromosomes (Solinas-Toldo et al., 1997; Pinkel et al., 1998; Pollack et al., 1999; Snijders et al., 2000). Relative copy number is then measured at these specific loci by hybridization of fluorescently labeled test and reference DNAs as in conventional CGN (Pinkel et al., 1998). Since the clones used on the array contain sequence tags, their positions are accurately known relative to the genome sequence, and genes mapping within regions of copy number alteration can be readily identified using genome databases.

Recently, array CGH has been used to identify DNA copy number variation in breast cancer tumors (Albertson, 2003). Albertson (2003), which provides useful information pertaining to array CGH techniques, is herein specifically incorporated by reference. In addition, alterations in DNA copy number in bladder tumors have been recently described (Veltman et al., 2003). Veltman et al., 2003, which also provides useful information pertaining to array CGH technology, is herein specifically incorporated by reference.

6. Quantitative Real Time PCR

Quantitative real-time PCR is based on the technique of polymerase chain reaction (PCR) and can determine gene duplications or deletions (Walker, 2002). Furthermore, small mutations, including single base changes, can be identified by melting curve analysis following PCR. Real-time polymerase chain reaction allows one to monitor the progress of the PCR as it occurs in real time. Therefore, the data is collected throughout the PCR process compared to regular PCR, which collects data at the end of the reaction. The real-time PCR product is detected during each amplification cycle by labeling the PCR product as it accumulates in each cycle with a highly specific, double-stranded fluorescent DNA binding dye. The amount of fluorescence is either directly or indirectly associated with the accumulation of the newly amplified DNA. The more rapid a significant increase in fluorescence is observed indicates a higher starting copy number of the nucleic acid target. The number of amplicons generated is directly proportional to the increase in the reporter fluorescent signal and amplicon detection is capable of detecting as small as a 2-fold change. Real-time PCR methods are becoming a favorable option for cancer marker analysis (Bernard, 2002). Recently, quantitative real-time PCR has been used to identify DNA copy number variation in breast cancer tumors (Konigshoff, 2003).

G. Pharmaceutical Preparations and Therapeutic Methods

1. Overview

The present invention generally concerns methods of making a pharmaceutical agent that modulates apoptosis, that includes the steps of obtaining one or more candidate substances, testing the one or more candidate substances to determine their ability to modulate the expression and/or function of 14-3-3 zeta, selecting a candidate substance determined to modulate the expression and/or function of 14-3-3 zeta, and making a pharmaceutical composition that includes the selected candidate substance. Certain other embodiments of the present invention involve methods of treating a subject with a hyperproliferative disease, that involve making a pharmaceutical agent by any of the methods set forth in this application, and administering the pharmaceutical agent to a subject.

2. Pharmaceutical Compositions

Pharmaceutical compositions of the present invention comprise an effective amount of a selected candidate substance that has been determined to modulate the expression and/or function of 14-3-3 zeta, dissolved or dispersed in a pharmaceutically acceptable carrier or aqueous medium. Aqueous compositions of selected candidate substances that are gene therapy vectors are also contemplated. The phrases "pharmaceutical composition" or "pharmacologically effective" or "pharmaceutically acceptable" refer to molecular entities and compositions that do not produce an adverse, allergic or other untoward reaction when administered to an animal, or a human, as appropriate.

As used herein, "pharmaceutical composition" includes the selected candidate substance, plus any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologics standards.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intralesional, or even intraperitoneal routes. The preparation of an aqueous composition containing an active agent of the invention disclosed herein as a component or active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An agent or substance of the present invention can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. In terms of using peptide therapeutics as active ingredients, the technology of U.S. Pat. Nos. 4,608,251; 4,601,903; 4,599,231; 4,599,230; 4,596,792; and 4,578,770, each incorporated herein by reference, may be used.

The carrier can also be a solvent or dispersion medium containing, for example, water, ethanol, polyol (for example, glycerol, propylene glycol, and liquid polyethylene glycol, and the like), suitable mixtures thereof, and vegetable oils.

The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infuision, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The active agents disclosed herein may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g., tablets or other solids for oral administration; liposomal formulations; time release capsules; and any other form currently used, including cremes.

One may also use nasal solutions or sprays, aerosols or inhalants in the present invention. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Additional formulations which are suitable for other modes of administration include vaginal suppositories and pessaries.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

3. Liposomes and Nanoparticles

The use of liposomes and/or nanoparticles is also contemplated for use in the pharmaceutical compositions of the present invention. The formation and use of liposomes is generally known to those of skill in the art, and is also described below.

Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

The following information may also be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

4. Dosage

Certain embodiments of the present invention pertain to methods of treating a subject with a hyperproliferative disease that involve administering a pharmaceutical agent of the present invention. An effective amount of the therapeutic or preventive agent is determined based on the intended goal, for example modulation of 14-3-3 activity. The quantity to be administered, both according to number of treatments and dose, depends on the subject to be treated, the state of the subject and the protection desired. Precise amounts of the therapeutic composition also depend on the judgment of the practitioner and are peculiar to each individual.

In certain embodiments, it may be desirable to provide a continuous supply of the therapeutic compositions to the patient. For topical administrations, repeated application would be employed. For various approaches, delayed release formulations could be used that provide limited but constant amounts of the therapeutic agent over an extended period of time. For internal application, continuous perfusion of the region of interest may be preferred. This could be accomplished by catheterization, post-operatively in some cases, followed by continuous administration of the therapeutic agent. The time period for perfusion would be selected by the clinician for the particular patient and situation, but times could range from about 1-2 hours, to 2-6 hours, to about 6-10 hours, to about 10-24 hours, to about 1-2 days, to about 1-2 weeks or longer. Generally, the dose of the therapeutic composition via continuous perfusion will be equivalent to that given by single or multiple injections, adjusted for the period of time over which the doses are administered.

Those of skill in the art are well aware of how to apply gene delivery to in vivo and ex vivo situations. For viral vectors, one generally will prepare a viral vector stock. Depending on the kind of virus and the titer attainable, one will deliver $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$ or $1 \times 10^{12}$ infectious particles to the patient. Similar figures may be extrapolated for liposomal or other non-viral formulations by comparing relative uptake efficiencies. Formulation as a pharmaceutically acceptable composition is discussed below.

5. Treatment of Artificial and Natural Body Cavities

One of the prime sources of recurrent cancer is the residual, microscopic disease that remains at the primary tumor site, as well as locally and regionally, following tumor excision. In addition, there are analogous situations where natural body cavities are seeded by microscopic tumor cells. The effective treatment of such microscopic disease would present a significant advance in therapeutic regimens.

Thus, in certain embodiments, a cancer may be removed by surgical excision, creating a "cavity." Both at the time of surgery and thereafter (periodically or continuously), the therapeutic composition of the present invention is administered to the body cavity. The volume of the composition should be sufficient to ensure that the entire surface of the cavity is contacted by the expression cassette.

In one embodiment, administration simply will entail injection of the therapeutic composition into the cavity formed by the tumor excision. In another embodiment, mechanical application via a sponge, swab or other device may be desired. Either of these approaches can be used subsequent to the tumor removal as well as during the initial surgery. In still another embodiment, a catheter is inserted into the cavity prior to closure of the surgical entry site. The cavity may then be continuously perfused for a desired period of time.

6. Tracers to Monitor Gene Expression Following Administration

Because destruction of microscopic tumor cells cannot be observed, it is important to determine whether the target site has been effectively contacted with the expression cassette. This may be accomplished by identifying cells in which the expression construct is actively producing the desired polypeptide product. It is important, however, to be able to distinguish between the exogenous polypeptide and that present in tumor and nontumor cells in the treatment area. Tagging of the exogenous polypeptide with a tracer element would provide definitive evidence for expression of that molecule and not an endogenous version thereof. Thus, the methods and compositions of the claimed invention may involve tagging of the polypeptide encoded by the expression cassette with a tracer element.

One such tracer is provided by the FLAG biosystem. The FLAG polypeptide is an octapeptide (Asp-TyrLysAspAspAspAspLys) and its small size does not disrupt the expression of the delivered gene therapy protein. The coexpression of FLAG and the protein of interest is traced through the use of antibodies raised against FLAG protein.

Other immunologic marker systems, such as the 6xHis system (Qiagen) also may be employed. For that matter, any linear epitope could be used to generate a fusion protein with the desired polypeptide so long as (i) the immunologic integrity of the epitope is not compromised by the fusion and (ii) the functional integrity of the desired polypeptide is not compromised by the fusion.

7. Secondary Treatment a. General

Certain embodiments of the claimed invention provide for a methods of treating a subject with cancer using one of the identified pharmaceutical agents of the present invention. In each of these embodiments, the subject may be receiving secondary antihyperplastic therapy. Examples of secondary antihyperplastic therapy include chemotherapy, radiotherapy, immunotherapy, phototherapy, cryotherapy, toxin therapy, hormonal therapy or surgery. Thus, the claimed invention contemplates use of the claimed methods and compositions in conjunction with standard anti-cancer therapies. The patient to be treated may be an infant, child, adolescent or adult.

A wide variety of cancer therapies, known to one of skill in the art, may be used in combination with the compositions of the claimed invention. Some of the existing cancer therapies and chemotherapeutic agents are described below. One of skill in the art will recognize the presence and development of other anticancer therapies which can be used in conjugation with the compositions comprising expression cassettes and will further recognize that the use of the secondary therapy of the claimed invention will not be restricted to the agents described below.

In order to increase the effectiveness of a an expression construct encoding a polypeptide that modulates 14-3-3 zeta activity, it may be desirable to combine these compositions with other agents effective in the treatment of hyperproliferative disease. These compositions would be provided in a combined amount effective to kill or inhibit proliferation of the cell. This process may involve contacting the cells with the expression construct and the agent(s) or second factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent.

Alternatively, the gene therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed. For example, the inhibitor of 14-3-3 zeta is therapy is "A" and the secondary agent, such as radio- or chemotherapy, is "B":

Administration of the therapeutic expression constructs of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described hyperproliferative cell therapy.

b. Radiotherapy

Radiotherapy include radiation and waves that induce DNA damage for example, $\gamma$-irradiation, X-rays, UV-irradiation, microwaves, electronic emissions, radioisotopes, and the like. Therapy may be achieved by irradiating the localized tumor site with the above described forms of radiations. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

In the context of the present invention radiotherapy may be used in addition to using the tumor cell specific-peptide of the invention to achieve cell-specific cancer therapy.

c. Surgery

Surgical treatment for removal of the cancerous growth is generally a standard procedure for the treatment of tumors and cancers. This attempts to remove the entire cancerous growth. However, surgery is generally combined with chemotherapy and/or radiotherapy to ensure the destruction of any remaining neoplastic or malignant cells. Thus, in the context of the present invention surgery may be used in addition to using the tumor cell specific-peptide of the invention to achieve cell-specific cancer therapy.

In the case of surgical intervention, the compositions of the present invention may be used preoperatively, to render an inoperable tumor subject to resection. Alternatively, the present invention may be used at the time of surgery, and/or thereafter, to treat residual or metastatic disease. For example, a resected tumor bed may be injected or perfused with a formulation comprising an expression construct. The perfusion may be continued post-resection, for example, by leaving a catheter implanted at the site of the surgery. Periodic post-surgical treatment also is envisioned.

In certain embodiments, the tumor being treated may not, at least initially, be resectable. Treatments with therapeutic viral constructs may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

A typical course of treatment, for a primary tumor or a post-excision tumor bed, will involve multiple doses. Typical primary tumor treatment involves a 6 dose application over a two-week period. The two-week regimen may be

```
A/B/A   B/A/B   B/B/A  A/A/B   A/B/B   B/A/A  A/B/B/B  B/A/B/B

B/B/B/A    B/B/A/B    A/A/B/B    A/B/A/B   A/B/B/A    B/B/A/A

B/A/B/A    B/A/A/B    A/A/B/B    B/A/A/A   A/B/A/A    A/A/B/A
``` repeated one, two, three, four, five, six or more times. During a course of treatment, the need to complete the planned dosings may be re-evaluated.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time. Unit dose of the present invention may conveniently may be described in terms of plaque forming units (pfu) for a viral construct. Unit doses range from $10^3$, $10^4$, $10^5$, $10^6$, $10^7$, $10^8$, $10^9$, $10^{10}$, $10^{11}$, $10^{12}$, $10^{13}$ pfu and higher.

d. Chemotherapeutic Agents

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate or any analog or derivative variant thereof. The term "chemotherapy" as used herein is defined as use of a drug, toxin, compound, composition or biological entity which is used as treatment for cancer. These can be, for example, agents that directly cross-link DNA, agents that intercalate into DNA, and agents that lead to chromosomal and mitotic aberrations by affecting nucleic acid synthesis.

Agents that directly cross-link nucleic acids, specifically DNA, are envisaged and are shown herein, to eventuate DNA damage leading to a synergistic antineoplastic combination. Agents such as cisplatin, and other DNA alkylating agents may be used.

Agents that damage DNA also include compounds that interfere with DNA replication, mitosis, and chromosomal segregation. Examples of these compounds include adriamycin (also known as doxorubicin), VP-16 (also known as etoposide), verapamil, podophyllotoxin, and the like. Widely used in clinical setting for the treatment of neoplasms, these compounds are administered through bolus injections intravenously at doses ranging from 25-75 mg/m$^2$ at 21 day intervals for adriamycin, to 35-100 mg/m$^2$ for etoposide intravenously or orally.

e. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with the expression cassette. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

f. Genes

In yet another embodiment, the secondary treatment is a gene therapy in which a different expression cassette than the one disclosed herein is administered before, after, or at the same time as the expression cassette of the claimed invention. Delivery may comprise use of a vector encoding polypeptide of the claimed invention in conjunction with a second vector encoding an additional gene product such as p53. Alternatively, a single vector encoding both genes may be used. A variety of secondary gene therapy proteins are envisioned within the invention.

g. Other Cancer Therapies

Examples of other cancer therapies include phototherapy, cryotherapy, toxin therapy, or hormonal therapy. One of skill in the art would know that this list is not exhaustive of the types of treatment modalities available for cancer and other hyperplastic lesions.

G. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

RNA interference of 14-3-3 zeta in mammalian cell culture. siRNA duplexes were synthesized based on a 14-3-3 zeta-specific sequence (SEQ ID NO:3) and a scrambled sequence (SEQ ID NO:4) by Darmacon Research Inc., CO. One million cells were seeded onto a 10-cm culture dish 24 hr prior to transfection in DMEM/F12 containing 10% FBS. 50 μl of siRNA duplexes (20 μM stock) were added to 750 μl Opti-MEM I (Invitrogen) containing 20 μl Plus Reagent (Invitrogen), mixed and incubated for 15 min at room temperature. Then 30 μl Lipofectamine (Invitrogen) was mixed and incubated with 750 μl Opti-MEM I. After incubation, two parts were mixed and incubated for another 15 min at room temperature. This combination was then assorted with 5 ml Opti-MEM I and added to cells that were pre-washed once with 5 ml Opti-MEM I. Five hours post-transfection, 6.5 ml of DMEM/F12 with 20% FBS were added to the cells. The transfection solution was removed 24 hours post-transfection and replaced with DMEM/F12 containing 10% FBS.

Immunohistochemical Staining of 14-3-3 zeta. 5 μm sections from formalin-fixed paraffin-embedded tissue block were deparaffinized and rehydrated. The slides were subjected to heat-induced epitope retrieval in 0.01 M citrate buffer (pH 6.0). After blocked for 30 min in 3% hydrogen peroxide, and then in normal horse serum for 20 min, the slides were incubated with 14-3-3 zeta antibody (C-16, Santa Cruz biotechnology, Santa Cruz, Calif.) at a dilution of 1:2000 for 30 min at room temperature. Immunodetection was performed with the LSAB2 system (DAKO, Carpinteria, Calif.). 3-3'-diaminobenzidine was used for color development, and hematoxylin was used for counterstaining.

Cytochrome C Staining. Mcf-7 cells were transfected with control or 14-3-3 zeta siRNA. Forty-eight hours post transfection cells were split to microscope slides. The next day, cells were replenished with serum free media. At 0 and 48 hours serum free, slides were fixed and stained with anti-cytochrome C (Pharmingen) followed by Alexa-Fluor 594 (Molecular Probes) secondary antibody and nuclei were stained with DAPI. Fluorescent signals were preserved by SlowFade Antifade Kit (Molecular Probes) and samples were analyzed by immunofluorescence microscopy and 2D-deconvolution (Tan et al., 2002). Cells with diffuse cytochrome C staining were counted as positive for cytochrome C release.

Western Blot Analysis. Sarcomas and normal tissues were homogenized in lysis buffer (PBS containing 1% Triton X-100, 0.5% sodium deoxycholate, 0.1% SDS, 100 µg/ml phenylmethylsulfonyl fluoride, and 0.02% sodium azide) followed by centrifugation at 12,000×g for 10 min at 4° C. to remove cell debris. Two hundred µg of protein from both tumor and normal samples were separated by SDS-PAGE (12% gel for p16 and CDK4 and 8% gel for RB) and transferred onto nitrocellulose membranes (Bio-Rad Laboratories, Hercules, Calif.). The membranes were blocked with 5% dried milk in TBS (0.05% Tween in PBS), probed with antibodies (1:1000 dilution), washed with TBS, and probed with proper secondary antibodies (against mouse IgG or rabbit IgG). Enhanced chemiluminescence was performed to detect the target protein on the membrane, according to the manufacturer's protocol (Amersham Corp., Arlington Heights, Ill.). To confirm the results in a stringent manner, membranes were stripped and reprobed with another antibody to the same proteins of interest (p16, CDK4, and RB).

Example 2

14-3-3 Zeta Expression is Elevated in Sarcomas and Primary Breast Cancer

A 29 kDa protein (p29) with a polyclonal anti-p16 antibody was detected in the sarcoma and primary breast cancer tissue specimens, presumably due to cross-reaction. Western blot analysis using anti-p16 antibody (which recognized p29) was performed in more than 50 soft tissue sarcoma samples. Interestingly, p29 expression was elevated in 60-70% of the sarcomas as well as in more than 70% primary breast tumors compared with autologous normal tissues. The p29 protein from a sarcoma specimen was purified to homogeneity. The p29 was purified by three steps: (a) preparative SDS-PAGE followed by gel extraction, (b) hydrophobic interaction chromatography, and (c) preparative HPLC. Purified p29 migrated as a single band of 29 kDa in a SDS-PAGE gel when stained by Coommassie blue. Microsequencing of in-gel digestion fragments of purified p29 revealed it as a known protein, 14-3-3 zeta. The identification was confirmed by immunoblotting analysis of sarcoma and breast tumors using a 14-3-3 zeta-specific antibody, which gave an expression patterns similar to p29.

Example 3

14-3-3 Zeta is Expressed in Multiple Tumor Types

IHC analysis of 14-3-3 zeta on a Tissue Array was conducted, which confirmed that 14-3-3 zeta was overexpressed in breast carcinoma. In addition, 14-3-3 zeta overexpression was detected in cancers of lung, liver, uterus, and stomach compared to their respective normal tissues. The tissue array slide from IMGENEX (cat# IMH-343/BA2) has 20 normal tissues and 19 different types of tumors (each tumor has one care) from human origin. The normal tissues include skin, breast, spleen, skeletal muscle, lung, liver, gallbladder, pancreas, stomach, small intestine, colon, rectum, kidney cortex, kidney medulla, bladder, prostate, uterus, placenta, umbilical cord, and fetal brain. The tumors include squamous cell carcinoma of the lung, bronchioloalveolar carcinoma of the lung, adenoid cystic carcinoma of the salivary gland, hepatocellular carcinoma, diffuse type adenocarcinoma of the stomach, intestinal type adenocarcinoma of the stomach, stromal sarcoma of the stomach, malignant lymphoma of the colon, mucinous carcinoma of the colon, adenocarcinoma of the rectum, malignant Schwanoma of the colon, renal cell carcinoma, poorly differentiated transitional carcinoma of the bladder, squamous cell carcinoma of the cervix, endometrial adenocarcinoma of the uterus, pheochromocytoma of the adrenal gland, metastatis adenocarcinoma of the liver (from bile duct), metastatic adenocarcinoma (from colon) of the ovary, and infiltrating ductal carcinoma of the breast. These results are further supported by immunoblot analysis showing that 14-3-3 zeta expression was elevated in many breast cancer, lung cancer, and sarcoma cell lines compared to normal breast and lung epithelial cell lines as well as in normal smooth muscle cells.

Example 4

14-3-3 Zeta Expression Enhances the Malignant Transformation of Cancer Cells

Elevated 14-3-3 zeta expression enhances the malignant transformation of breast cancer cells. MDA-MB-435 breast cancer cells were transfected with an expression vector for hemagglutinin (HA)-tagged 14-3-3 zeta and established pooled stable transfectants (435.1433 zeta) expressing exogenous 14-3-3 zeta. The 435.1433 zeta cells did not exhibit enhanced cell growth under normal culture conditions (data not shown). However, in soft agar colony formation assays, the increase of 14-3-3 zeta in 435.1433 zeta cells led to a moderate increase of transforming colonies with 10% serum and a more dramatic increase of colonies without serum (FIG. 1A). This indicates that 14-3-3 zeta can enhance the anchorage-independent growth of cancer cells. Additionally, elevated expression of 14-3-3 zeta conferred MDA-MB-435 cells resistance to γ-radiation-induced apoptosis (FIG. 1B).

Example 5

Blocking 14-3-3 Zeta Expression Inhibits Malignant Transformation of Cancer Cells To further investigate the role of 14-3-3 zeta in cancer progression and to determine whether blocking 14-3-3 zeta expression would inhibit malignant transformation and cancer development, small interfering RNA (siRNA) duplexes were used to specifically silence the expression of 14-3-3 zeta in multiple cancer cell lines. After 24 hours of transfection, the 14-3-3 zeta siRNA efficiently inhibited 14-3-3 zeta expression without affecting the expression of 14-3-3 beta, the 14-3-3 isoform most homologous to 14-3-3 zeta. This inhibition effect of 14-3-3 zeta siRNA could persist for approximately 6-7 days.

14-3-3 zeta siRNA-treated cells displayed dramatic morphology changes with cellular shrinkage and membrane blebbing, phenotypes characteristic of apoptotic cells, while the control siRNA-treated cells showed no morphology changes under the same experimental conditions. Cell growth rate assays revealed approximately 50% growth inhibitions in MDA-MB-435 and MCF-7 cells treated with 14-3-3 zeta siRNA compared to those treated with the control siRNA in both 10% and 0.5% serum (FIG. 1C, and data not shown). This was at least partly due to an increase in cells arrested at the $G_1$ phase of the cell cycle in 14-3-3 zeta siRNA-treated cells, as shown by fluorescence-activated cell sorter (FACS) analysis of two breast cancer cell lines, a cervical carcinoma cell line (HeLa), and a lung cancer cell line (H1299) after 14-3-3 zeta siRNA treatment (FIG. 1D). Further studies were conducted to determine whether 14-3-3 zeta siRNA alters the expression of $G_1$ phase cell cycle regulators. Compared to the control siRNA-treated cells, 14-3-3 zeta siRNA-treated cells exhibited a marked increase in $p_{27}^{KIP1}$ and $p21^{CIP1}$ expression, whereas $p16^{INK4a}$ and Cyclin D1 expression were not changed significantly except in H1299. Therefore, the $G_1$ arrest from 14-3-3 zeta silencing may result from up-regulating the cyclin-dependent kinase inhibitors $p27^{KIP1}$ and $p21^{CIP1}$. Similar results were observed when cells are treated with another 14-3-3 zeta siRNA duplex targeting a different mRNA region (data not shown).

Example 6

14-3-3 Zeta is Involved in the Stress-Induced Apoptotic Response

Figure 2:
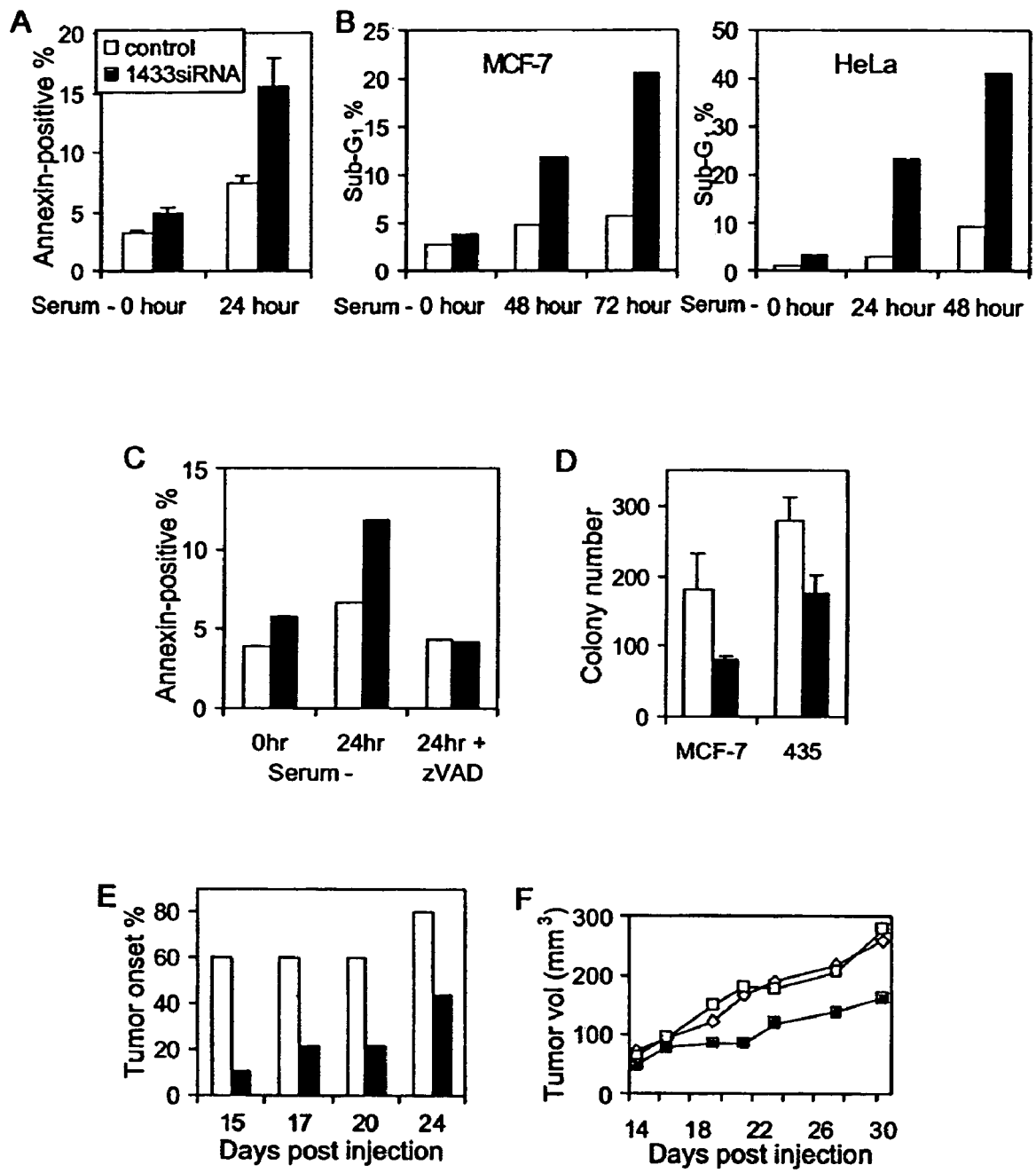
FIG. 2A, FIG. 2B, FIG. 2C, FIG. 2D, FIG. 2E, FIG. 2F. Silencing 14-3-3 zeta by siRNA sensitizes cells to stress-induced apoptosis and reduces tumorigenic properties of breast cancer cells.

Studies were conducted to investigate the role of 14-3-3 zeta in stress-induced apoptotic responses. Under serum starvation conditions, MCF-7 and HeLa cells treated with 14-3-3 zeta siRNA showed a remarkable increase in apoptotic annexin-positive (FIG. 2A) and sub-$G_1$ (FIG. 2B) populations compared to cells treated with control siRNA, indicating that silencing of 14-3-3 zeta sensitized these cancer cells to stress-induced apoptosis. To understand the underlying mechanisms, the activation of two major apoptosis pathways (death receptor pathway and mitochondria pathway; Wajat, 2002) in cancer cells was investigated after 14-3-3 zeta siRNA treatment. While no significant difference in Fas activation was found between 14-3-3 zeta siRNA and control siRNA-treated cells (data not shown), immunostaining of cytochrome C clearly demonstrated its release from mitochondria in 14-3-3 zeta siRNA-treated MCF-7 cells after serum withdrawal. Immunoblot analysis of caspase-9 showed a decrease of pro-caspase-9 in 14-3-3 zeta siRNA-treated cells, indicative of activation of caspase-9 by proteolytic cleavage. An examination of downstream caspase substrates such as poly (ADP-ribose) polymerase (ARP) and $p_{130}^{CAS}$ also revealed their cleavage in 14-3-3 zeta siRNA-treated cells. Thus, downregulation of 14-3-3 zeta could sensitize cancer cells to apoptosis through activation of the mitochondria pathway. Moreover, an increased BAD expression was detected in 14-3-3 zeta siRNA-treated cells. BAD is a known 14-3-3 ligand and a pro-apoptotic molecule facilitating cytochrome C release. It was therefore proposed that downregulation of 14-3-3 zeta increases BAD protein levels through yet undefined mechanisms leading to increased cytochrome C release and subsequent caspase activation. Furthermore, addition of a caspase inhibitor (Z-VAD-FMK) to the 14-3-3 zeta siRNA-treated MCF-7 cells in serum-free media effectively blocked PARP cleavage and 14-3-3 zeta siRNA failed to sensitize these cells to stress-induced apoptosis (FIG. 2C). Therefore, the sensitization to stress-induced apoptosis by 14-3-3 zeta siRNA may require sequential events, involving the up-regulation of BAD, increased cytochrome C release, caspase activation, and caspase substrate cleavages.

Downregulation of 14-3-3 zeta also inhibited the transforming properties of cancer cells, as 14-3-3 zeta siRNA-treated MDA-MB-435 and MCF-7 cells formed less soft agar colonies than the control group (FIG. 2D). This indicated the potential of targeting 14-3-3 zeta in blocking malignant transformation. To test this, MDA-MB-435 cells were transfected with 14-3-3 zeta siRNA or control siRNA, and then cells were injected into the mammary fat pads (mfp) of female SCID mice. The mice in the 14-3-3 zeta siRNA group demonstrated markedly delayed tumor onset and reduced tumor growth (FIG. 2E, FIG. 2F), which paralleled with 14-3-3 zeta reduction, $p27^{KIP1}$ upregulation, and increased TUNEL positive apoptotic cells in the tumors grown in the mfp. Thus, a brief blockage of 14-3-3 zeta was sufficient to suppress tumorigenicity of MDA-MB-435 breast cancer cell line in vivo.

Example 7

Figure 3:
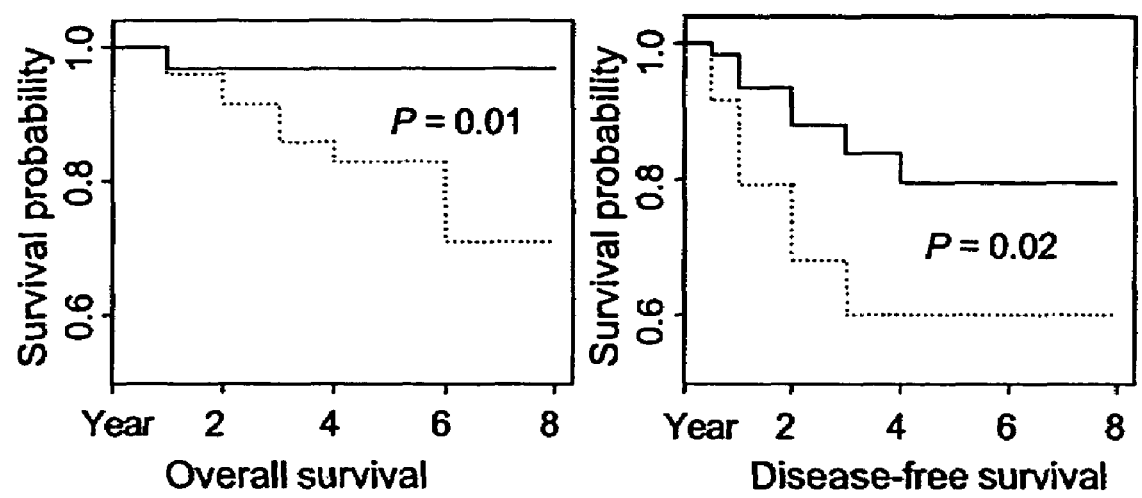
FIG. 3. Overexpression of 14-3-3 zeta correlates to poor survival in breast cancer patients. 14-3-3 zeta protein expression was measured by immunohistochemical (IHC) analysis in primary invasive breast carcinomas from 107 patients, who had chemotherapies after mastectomy, with a median follow-up time of 72 months. Representative 14-3-3 zeta IHC staining in breast cancer specimens (n=107) was graded as negative, weakly positive, moderately positive, or strongly positive for 14-3-3 zeta overexpression. Benign breast epithelial cells and stromal components were negative or weakly positive for 14-3-3 zeta staining. Overall and disease-free survival curve of patients with tumors having low (negative, weak, moderately positive) (—) (n=59) or high (strongly positive) (---) (n=48) 14-3-3 zeta expression.

14-3-3 Zeta Expression Provides Prognostic Information in Patients with Cancer 14-3-3 zeta is a biomarker for poor prognosis of breast cancer. To further investigate the impact of 14-3-3 zeta overexpression on cancer progression in patients, IHC analysis of 14-3-3 zeta was performed in primary invasive breast carcinomas from 107 patients, who were treated with cyclophosphamide, methotrexate, and 5-fluorouracil after mastectomy with a median follow-up time of 62 months (Yang et al., 2002). Among these patients' samples, 22 were negative or weakly positive for 14-3-3 zeta expression, whereas 89 were moderately or strongly positive, i.e., had 14-3-3 zeta overexpressions to different extents. Positive 14-3-3 zeta signals were observed mainly in the cytoplasm of the breast carcinoma cells, whereas benign breast epithelial cells and stromal components were negative or weakly positive for 14-3-3 zeta staining under the same experimental conditions. Using Kaplan-Meier analyses, high 14-3-3 zeta scores in breast tumors (n=48) are significantly associated with reduced disease-free survival (P=0.02) and reduced overall survival (P=0.01) (FIG. 3). Thus, 14-3-3 zeta is a biomarker for poor prognosis of breast cancers. Compared to known poor prognostic markers such as HER2 or uPA overexpression, 14-3-3 zeta strong positive staining were observed in more patients (approximately 45% for 14-3-3ζ compared to 30% for HER2 and 15% for uPA (Rogers et al., 2002). Therefore, monitoring 14-3-3 zeta protein levels in breast cancer specimens may provide additional prognostic information to the current clinical and pathological parameters.

In this study, it has been demonstrated that 14-3-3 zeta is overexpressed in multiple human primary tumors and cancer cell lines representing a frequent event in cancer development of a broad spectrum of cancer types. Downregulation of 14-3-3 zeta led to $G_1$ arrest by upregulation of $p27^{KIP1}$ and $p21^{CIP1}$ in all cancer cells examined, indicating that 14-3-3 zeta may be a key factor utilized by many types of cancer cells to control certain common pathways during cancer progression. Mechanisms underlying 14-3-3 zeta ablation-induced p27$^{KIP1}$ and p21$^{CIP1}$ upregulation are currently under investigation. Downregulation of 14-3-3 zeta also sensitizes cancer cells to apoptosis, indicating 14-3-3 zeta plays an essential role in cancer cell survival and 14-3-3 zeta might be used as a predictive marker for response to chemotherapy in cancer patients. A brief blockade of 14-3-3 zeta expression by siRNA (up to 7 days) considerably inhibited tumor onset and tumor growth from breast cancer cells in vivo, signifying 14-3-3 zeta is an attractive therapeutic target in human cancers. The significant association between 14-3-3 zeta overexpression and poor survival of breast cancer patients further demonstrates the clinical potential of 14-3-3 zeta as a prognostic marker and a therapeutic target.

Example 8

14-3-3 Zeta Gene Amplification is Correlated with its Overexpression in Cancer Patients Based on the study on samples from normal tissues, criteria were set up for 14-3-3 zeta gene amplification as the following. The upper limit cut-off value was set to the mean+3 SD of the technical variation found in the analysis of 10 normal breast tissue samples. Samples with less than 19% of cells having >2 copies of 14-3-3 zeta gene per cell were classified as "normal"; samples with 19% or more cells having >2 copies, the average copy number being between 2 and 5, and the ratio of 14-3-3 zeta to chromosome 8 being $\geq 1$ were classified as "low"; samples with more than 19% cells having >2 copies, the average copy number being $\geq 5$, and the ratio of 14-3-3 zeta to chromosome $8 \geq 1$ were regarded as "high." Forty-three breast cancers were analyzed for the 14-3-3 zeta gene and the chromosome 8 centromere using dual-color FISH. 11/43 (25.6%) of samples were normal, 9/43 (20.9%) of samples were low, and 22/43 (51.2%) of samples showed high amplification. In about 70% of cases, there is a correlation between 14-3-3 zeta gene amplification and protein expression.

Example 9

14-3-3 Zeta Interacts With PI3-Kinase

Methods 14-3-3 zeta stable transfections. To generate 14-3-3 zeta stable transfectants, one million cells were seeded onto a 100 mm tissue culture plate 24 hours prior to transfection in DMEM/F12 medium containing 10% FBS. MCF-7 and MDA-MB-435 breast cancer and H1299 lung cancer cell lines were used to generate HA-tagged 14-3-3 zeta stable transfectants. P85 stable transfectants were made by stably transfecting both HA-14-3-3 zeta and the HIS-tagged p85 contructs in the MCF-7 breast cancer cell line.

10 μg of DNA were added to 750 μl of Opti-MEM I (Invitrogen) containing 20 μl of Plus Reagent (Invitrogen), mixed and incubated for 15 minutes at room temperature. At the same time, 30 μl of Lipofectamine (Invitrogen) were mixed and incubated with 750 μl of Opti-MEM I. After incubation, the two parts were mixed and incubated for another 15 minutes at room temperature. This combination was diluted with 5 ml of Opti-MEM I and added to cells that were pre-washed once with 5 ml of Opti-MEM I. Five hours post-transfection, 6.5 ml of DMEM/F12 media with 20% FBS were added to the cells. The transfection solution was removed 24 hours post-transfection and replaced with DMEM/F12 medium containing 10% FBS. At 48 hours post transfection, cells were split to a very light density in 100 mm tissue culture plates and media containing 800 μg/mL of G418 drug selection. Cells were maintained in selection media until single colonies of cells formed in the dish. Multiple colonies were selected, expanded and screened for the expression of HA-14-3-3 zeta protein by Western blot analysis. Clones with the highest expression were selected and expanded further.

Western Blot Analysis. Proteins were separated and analyzed by harvesting cells in 500 μl or less of 14-3-3 zeta lysis buffer (50 mM Tris-HCl pH 7.5, 150 mM NaCl, 2 mM EGTA, 2 mM MgSO$_4$, 0.1% Tween-20, protease cocktail inhibitor, 1 mM PMSF, 20 mM NaF, 1 mM Na$_3$VO$_4$, 20 mM β-glycerophosphate) and allowed to incubate on ice for 20 minutes or stored at −80° C. until used. Cells were further lysed by six passes through a 22 gauge needle. Cellular debris was pelleted by centrifugation at 14000 rpm for 15 minutes at 4° C. The supernatant was transferred to a new tube and the Bradford Method determined protein concentration. The indicated amount of protein lysate was resuspended in 6×SDS lysis buffer and heated at 100° C. for 5 minutes. The lysate was then separated by SDS-PAGE. The proteins were transferred to a nitrocellulose membrane and probed with the respective antibodies.

Immunoprecipitation. To determine protein—protein association, cells were harvested in 14-3-3 zeta lysis buffer (50 OM Tris-HCl pH 7.5, 150 mM NaCl, 2 mM EGTA, 2 mM MgSO$_4$, 0.1% Tween-20, protease cocktail inhibitor, 1 mM PMSF, 20 mM NaF, 1 mM Na$_3$VO$_4$, 20 mM β-glycerophosphate) and allowed to incubate on ice for 20 minutes. Cells were further lysed by six passes through a 22 gauge needle. Cellular debris was pelleted by centrifugation at 14000 rpm for 15 minutes at 4° C. The supernatant was transferred to a new tube and the Bradford Method determined protein concentration. Immunoprecipitation (IP) was performed by adding the indicated antibodies to 1 mg of total cellular lysate which was incubated overnight at 4° C. In some cases, cell lysates were pre-cleared by incubating 30 μl of protein G beads with lysate for 1 hour and recovering lysate to a new tube. After incubation with antibody, 40 μl of protein G agarose beads were added and incubated for 2 hours more to pull down immune complexes. Beads with attached antibodies and proteins were recovered by centrifugation at 5000 rpm at 4° C. followed by five washes with lysis buffer. The bead complexes were then used in other assays or resuspended in 30 μl of lysis buffer with 5 μl of 6×SDS loading dye and analyzed by Western blot analysis.

PI3K Assay. To determine the activity of PI3K from MCF-7 cells treated with siRNA, cells were serum starved for 18 hours. Where indicated, cells were re-stimulated with 20 ng/ml of Heregulin for 10 minutes. Cells were lysed and immunoprecipitated with 1 μg of phosphotyrosine-20 antibody (Signal Transduction Laboratories, Inc.). Immune complexes were washed three times with lysis buffer and once with kinase buffer (20 mM Tris-HCl, pH 7.5, 100 mM NaCl, and 0.5 mM EGTA). The beads were resuspended in 50 μl of kinase buffer with 0.2 mg/ml of phosphatidylinositol. Then 20 μCi of [γ-$^{32}$P]ATP and 20 mM MgCl$_2$ were added for 10 minutes at room temperature. Reactions were terminated by adding 150 μl of chloroform/methanol, and phosphatidylinositol was extracted with 100 μl of chloroform. The organic phase was washed with methanol/1M HCL (1:1) and lyophilized. Following reusepension in 15 μl of chloroform, phosphatidylinositol was spotted on a silica gel 60 thin layer chromatography plate and resolved in chloroform/methanol/28% ammonium hydroxide/water (86:76:10:14) for 45 minutes. Phosphorylated products were visualized by autoradiography.

Induction of Akt activity. To determine the contribution of 14-3-3 zeta to Akt activation, $1 \times 10^6$ cells stably expressing full length 14-3-3 zeta or C-terminal deleted 14-3-3 zeta were plated in 100 mm tissue culture plates and allowed to attach overnight. Cells were washed three times with serum free media and replenished with serum free media. Cells were starved for 18 hours and either left unstimulated or stimulated for 10 minutes with media containing 10% FBS. Treated cells were washed once with 5 mL of 1×PBS and harvested in 14-3-3 zeta lysis buffer. Lysates were analyzed as in Western blot analysis with the indicated phospho-specific antibodies and reprobed with the native antibody as a loading control.

Site Directed Mutagenesis of p85. To change the amino acid serine 83 to alanine on p85, a p85 expression vector containing the p85 cDNA was used as the mutagenesis template. The QuickChange site directed mutagenesis kit from Stratagene (La Jolla, Calif.) was used to carry out the mutagenesis of p85 according to the manufactures protocol. Sequencing of the mutated plasmid was used to confirm the amino acid change in the expression plasmid.

TUNEL Assay for measurement of apoptosis. For analysis of apoptosis using terminal deoxynucleotide transferase dUTP nick end labeling (TUNEL), $6 \times 10^5$ cells were plated in 60 mm tissue culture plates and allowed to attach overnight. Apoptosis was induced in the cells by serum free conditions and collected at the designated times. Cells were harvested into a 15 mL tube by collecting the media from the plate, which includes floating cells, and trypsinizing the attached cells. Cells were pelleted by centrifugation at 1200 rpm. The pellet was washed with 3 mL of 1×PBS and then resuspended in 1% paraformaldehyde in PBS and placed on ice for 30 minutes. Cells were pelleted and washed with 1×PBS and then resuspended in 70% ethanol and placed overnight at −20° C. Apoptosis was detected using the APO-BRDU kit from Phoenix Flow Systems (San Diego, Calif.) following the manufacturer's protocol. Briefly, fixed cells were pelleted and washed twice with 1 mL of Wash buffer. Cells were then resuspended in 50 µl of DNA Labeling Solution (TdT reaction buffer, Tdt enzyme and Br-dUTP) and incubated at 37° C. for 3 hours. After incubation, 1 mL of Rinse buffer was added to the reaction and cells were pelleted and washed again in Rinse buffer. The cells were resuspended in 100 µl of Antibody Solution and incubated in the dark at room temperature for 2 hours. Cells were stained with Propidium Iodide/RNase A solution and analyzed by flow cytometry.

Results 14-3-3 zeta associates with phosphatidylinositol-3-kinase (PI3K) in cancer cells. The previous results indicate that blocking 14-3-3 zeta in cancer cells by siRNA sensitizes these cells to apoptosis and reduces their growth. This indicates that 14-3-3 zeta mediates an essential survival and growth signal within cancer cells. Phosphatidylinositol-3-kinase (PI3K) and its down stream signaling molecule Akt regulate apoptosis and cell growth in many cell types (Vivanco and Sawyers, 2002). Other studies using hematopoietic cells have suggested 14-3-3 may modulate PI-3K; however, the role of 14-3-3 in regulating PI3K is not established in cancer cells (Guthridge et al., 2000; Munday et al., 2000). Therefore, it is hypothesized that 14-3-3 zeta could associate with PI3K and modulate PI3K activity in human cancer cells to mediate survival signals and growth.

Figure 4:
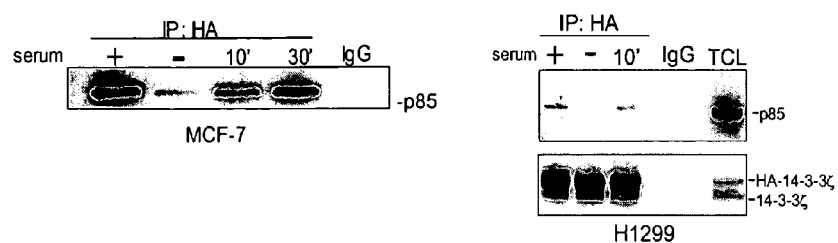
FIG. 4A, FIG. 4B, FIG. 4C, FIG. 4D. 14-3-3 zeta binds to p85 and modulates PI3K activity and Akt activation.
Figure 4:
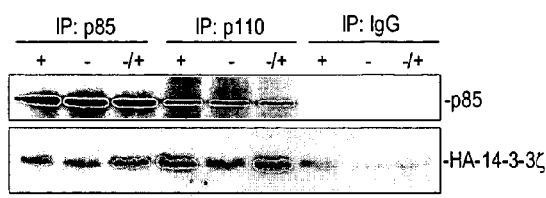
Figure 4:
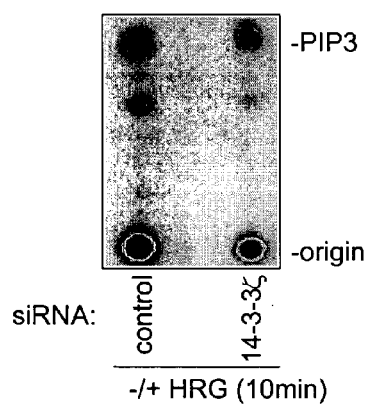
Figure 4:
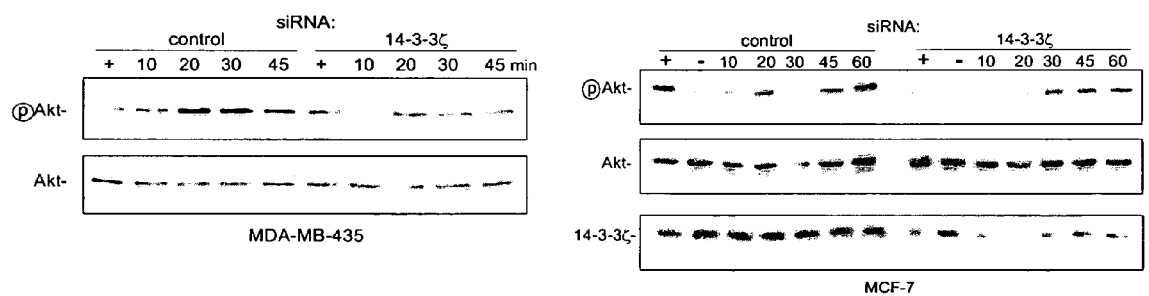

Immunoprecipitation of HA-14-3-3 zeta from MCF-7 cells stably transfected with a HA-14-3-3 zeta expression vector pulled down the endogenous p85 subunit in 10% serum conditions but not in cells deprived of serum (FIG. 4A, left). It was then determined if this association was serum dependent by starving these cells and then re-stimulating them with 10% serum. Association of HA-14-3-3 zeta and endogenous p85 could be restored 10 minutes after serum addition (FIG. 4A, left). This same pattern was also demonstrated in the H1299 lung cancer cell line stably transfected with HA-14-3-3 zeta (FIG. 4A, right). In addition, immunoprecipitation of either the endogenous p85 or p110 subunit demonstrated association with HA-14-3-3 zeta (FIG. 4B). The results indicate that 14-3-3 zeta associates with PI-3K in a serum dependent manner and suggests 14-3-3 zeta may be involved in PI3K activation by growth factors in the serum.

14-3-3 zeta modulated phosphatidylinositol-3-kinase (PI3K) activity. The association of p85 regulatory subunit and p110 catalytic subunit is required for PI3K activity (Cantley, 2002) and 14-3-3 binding to PI3K may modulate its activity. Therefore, it was hypothesized that 14-3-3 zeta association with p85 could enhance PI3K kinase activity in breast cancer cells. To investigate if PI-3K activity was modulated by 14-3-3 zeta, MCF-7 cells were transfected with control or 14-3-3 zeta siRNA. Cells were starved and then stimulated with the growth factor, Heregulin. MCF-7 14-3-3 zeta siRNA treated cells indeed exhibited reduced activation of PI3K in response to Heregulin stimulation compared to control siRNA treated cells (FIG. 4C). The data indicated that silencing of 14-3-3 zeta reduced PI-3K activation by growth factor.

Blocking 14-3-3 zeta inhibited Akt activation. PI3K is a well-known upstream activator of the survival signaling kinase, Akt (Vivanco and Sawyers, 2002). The Akt kinase is known to regulate signaling pathways involved in cell survival and proliferation (Vivanco and Sawyers, 2002). PI3K converts phosphatidylinositol 4,5-bisphosphate (PIP2) to phosphatidylinositol 3,4,5-trisphosphate (PIP3) in the cell membrane. The lipid by-product PIP3, generated by PI3K, activates Akt (Cantley, 2002). These results demonstrate that blocking 14-3-3 zeta reduces PI3K activity thereby reducing the production of PIP3 in the cells. Therefore, downregulation of 14-3-3 zeta may affect downstream cell survival pathways by inhibiting Akt activity. To test this hypothesis, MDA-MB-435 and MCF-7 cells were transfected with control or 14-3-3 zeta siRNA, serum starved, or starved then stimulated with 10% serun for various times (FIG. 4D). Activation of Akt, as measured by Akt phosphorylation using phospho-serine473-Akt specific antibody, was reduced by 14-3-3 zeta siRNA compared to the control MDA-MB-435 cells. In the controls, Akt was dramatically activated 20 minutes and remained elevated after serum addition compared to the basal (+). In contrast, activation of Akt in cells treated with 14-3-3 zeta siRNA was minimal at 20 minutes and did not increase by 45 minutes. A similar trend was demonstrated in the MCF-7 cell line. In the MCF-7 controls, Akt was activated 20 minutes after serum addition and remained elevated up to 60 minutes. In contrast, activation of Akt was reduced during this same time period in 14-3-3 zeta siRNA treated cells. These results indicate that 14-3-3 zeta regulates the signaling pathway involved in Akt activation partly by regulating the kinase activity of PI3K.

Figure 5:
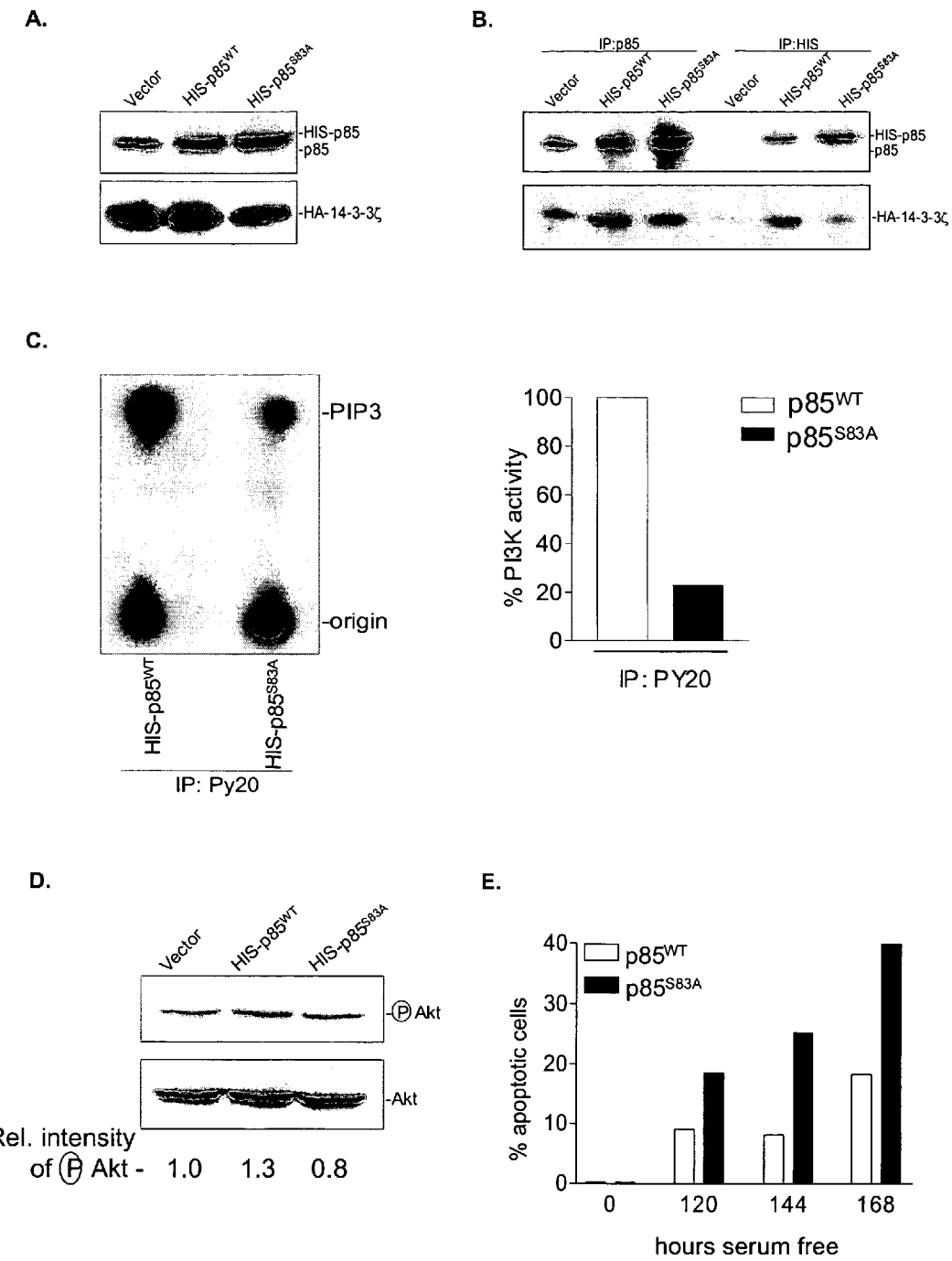
FIG. 5A, FIG. 5B, FIG. 5C, FIG. 5D, FIG. 5E. Mutation of serine 83 on p85 reduces 14-3-3 zeta association, reduces PI3K activity and sensitizes cells to apoptosis under serum-free conditions.

Serine 83 of p85 is necessary for 14-3-3 zeta association, PI3K activation and anti-apoptosis. It was next determined whether 14-3-3 zeta binding to p85 is critical for 14-3-3 zeta's effects on PI3K/Akt activation and anti-apoptosis by disrupting the binding of 14-3-3 zeta to p85. Most 14-3-3 zeta binding partners contain at least one consensus 14-3-3 zeta binding site that consists of a phosphorylated serine residue (Rittinger et al., 1999). Analysis of the p85 protein sequence revealed a possible consensus 14-3-3 zeta binding site surrounding serine 83 of p85. Using site directed mutagenesis, serine 83 of p85 was mutated to alanine (S83A). MCF-7 cells expressing HA-14-3-3 were then stably transfected with expression vectors encoding histidine tagged wild type p85 ($p85^{wt}$) and p85 with serine 83 to alanine ($p85^{S83A}$). Expression of these constructs in MCF-7 cells achieved proteins levels similar to endogenous p85 (FIG. 5A). To determine if association was reduced between 14-3-3 zeta and $p_{85}^{S83A}$, stable MCF-7 cells were serum starved for 18 hours and then stimulated with 10% serum media for 10 minutes. Cells were lysed and immunoprecipated (IP) with antibodies to p85 and to HIS-tag on p85, then western blot with anti-HIS and anti-HA to determine IP efficiency and 14-3-3 zeta binding. HA-14-3-3 zeta association with $p85^{S83A}$ was greatly reduced compared to $p85^{WT}$ in both p85 and HIS IP (FIG. 5B). The data indicate that 14-3-3 zeta associates with p85, at least partly through binding to serine 83 on p85. Furthermore, mutation of serine 83 on p85 reduced activation of PI3K by 35% compared to $p_{85}^{WT}$ in cells maintained in 10% serum media (FIG. 5C). In addition, activation of Akt was reduced in $p_{85}^{S83A}$ cells maintained in 10% serum media (FIG. 5D). Apoptosis induced by serum starvation was also elevated in cells expressing $p85^{S83A}$ compared to $p85^{WT}$ (FIG. 5E). These results indicate that 14-3-3 zeta associates with p85 through serine 83 thereby modulating PI3K/Akt activation and cell survival in response to stress induced apoptosis.

14-3-3 zeta interacts with both the p85 and p110 subunits of PI3-kinase. Interaction between 14-3-3 zeta and PI3-kinase were examined by immunoprecipitation followed by western blot analysis. MCF-7 and H1299 cells were stably transfected with an HA-14-3-3 zeta expression vector. Immunoprecipitation of HA-tagged 14-3-3 zeta effectively brought down p85 subunit in a phosphorylation-dependent manner. On the other hand, immunoprecipitation of either p85 or p110 subunit also brought down HA-14-3-3 zeta, as revealed by western blot using HA antibodies.

Example 10

Assays to Identify Modulators of Death of a Cancer Cell

Using the teachings of the specification and the knowledge of those skilled in the art, one can conduct assays to identify modulators of death of a cancer cell. Candidate substances suspected of modulating 14-3-3 zeta activity can first be identified. The candidate substance may include, but are not limited to, small molecules, peptides, polypeptides, proteins, nucleic acids, or any molecule suspected of modulating 14-3-3 zeta activity. The candidate substance may then be contacted with the cancer cell, and modulation of death of the cancer cell can be measured. Any method known to those of skill in the art can be used to contact the candidate substance with the cancer cell. For example, the candidate substances can be applied to a culture of cancer cells in vitro. Alternatively, animal models of cancer well known to those of skill in the art can be used in these assays to identify modulators of death of a cancer cell. Modulation of cell death can include either an increase in cell death, or an inhibition of cell death relative to a control cell that has not been contacted with the candidate substance.

Example 11

Clinical Trials of the Use of Modulators of 14-3-3 Zeta Expression and/or Function in the Treatment of Diseases in General This example is generally concerned with the development of human treatment protocols using modulators of 14-3-3 zeta expression and/or function in the treatment of diseases, such as hyperproliferative diseases. Examples of these diseases include cancer, such as breast cancer. A more detailed example pertaining to cancer is discussed in the next example.

The various elements of conducting a clinical trial, including patient treatment and monitoring, will be known to those of skill in the art in light of the present disclosure. The following information can be used as a general guideline for use in administering modulators of 14-3-3 zeta expression and/or function in clinical trials.

Patients with the targeted disease can be newly diagnosed patients or patients with existing disease. Patients with existing disease may include those who have failed to respond to at least one course of conventional therapy.

The modulator of 14-3-3 zeta activity may be a substance that either inhibits 14-3-3 zeta expression and/or function, or alternatively may be a substance that promotes 14-3-3 zeta expression and/or function. The modulator may be administered alone or in combination with another therapeutic agent. The agents may be administered intravenously, orally, topically, intratumorally, or by another mechanism that is specific to the disease that is being treated. The agent may be administered during a procedure, such as intraoperatively.

One of ordinary skill in the art would determine an appropriate starting dose, or the starting dose would be dictated by a clinical protocol. Dose escalation may be done by 100% increments until drug related toxicity of a specific level develops. Thereafter dose escalation may proceed by 25% increments. The administered dose may be fractionated.

The modulator of 14-3-3 zeta activity may be administered over a short infusion time or at a steady rate of infusion over a period of days. The modulator may be administered alone or in combination with other agents. The infusion given at any dose level will be dependent upon the toxicity achieved after each.

Physical examination, laboratory tests, and other clinical studies specific to the disease being treated may, of course, be performed before treatment and at intervals of about 3-4 weeks later. Laboratory studies can include CBC, differential and platelet count, urinalysis, SMA-12-100 (liver and renal function tests), coagulation profile, and any other appropriate chemistry studies to determine the extent of disease, or determine the cause of existing symptoms. If necessary, appropriate biological markers in serum can be monitored.

Example 12

Clinical Trials of the Use of Modulators of 14-3-3 Zeta Activity in the Treatment of Cancer This example is concerned with the development of human treatment protocols using modulators of 14-3-3 zeta activity in the treatment of cancer. The various elements of conducting a clinical trial, including patient treatment and monitoring, will be known to those of skill in the art in light of the present disclosure. The following information can be used as a general guideline for use in administering modulators of 14-3-3 zeta activity in clinical trials pertaining to cancer treatment.

Patients with cancer chosen for clinical study will typically have failed to respond to at least one course of conventional therapy. Measurable disease is not required.

The modulator of 14-3-3 zeta activity may be administered alone or in combination with another chemotherapeutic agent. The administration may be intravenously, directly into the tumor, topically, or in any other manner known to those of skill in the art. The starting dose may be 0.5 mg/kg body weight. Three patients may be treated at each dose level in the absence of grade >3 toxicity. Dose escalation may be done by 100% increments (0.5 mg, 1 mg, 2 mg, 4 mg) until toxicity is detected. Thereafter dose escalation may proceed by 25% increments.

The modulator of 14-3-3 zeta activity may be administered over a short infusion time or at a steady rate of infusion over a 7 to 21 day period. The modulator may be administered alone or in combination with the anti-cancer drug. The infusion given at any dose level will be dependent upon the toxicity achieved after each. Increasing doses of the modulator of 14-3-3 zeta activity in combination with an anti-cancer drug will be administered to groups of patients until approximately 60% of patients show unacceptable toxicity. Doses that are 2/3 of this value could be defined as the safe dose.

Physical examination, tumor measurements, and laboratory tests can, of course, be performed before treatment and at intervals of about 3-4 weeks later. Laboratory studies should include CBC, differential and platelet count, urinalysis, SMA-12-100 (liver and renal function tests), coagulation profile, and any other appropriate chemistry studies to determine the extent of disease, or determine the cause of existing symptoms. Also appropriate biological markers in serum can be monitored.

To monitor disease course and evaluate the anti-tumor responses, it is contemplated that the patients may be examined for appropriate tumor markers every 4 weeks, if initially abnormal. Laboratory studies such as a CBC, differential and platelet count, coagulation profile, and/or SMA-12-100 shall be performed weekly. Appropriate clinical studies such as radiological studies should be performed and repeated every 8 weeks to evaluate tumor response.

Clinical responses may be defined by acceptable measure. For example, a complete response may be defined by the disappearance of all measurable disease for at least a month. Whereas a partial response may be defined by a 50% or greater reduction of the sum of the products of perpendicular diameters of all evaluable tumor nodules or at least 1 month with no tumor sites showing enlargement. Similarly, a mixed response may be defined by a reduction of the product of perpendicular diameters of all measurable lesions by 50% or greater with progression in one or more sites.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. 4,578,770
U.S. Pat. 4,596,792
U.S. Pat. 4,599,230
U.S. Pat. 4,599,231
U.S. Pat. 4,601,903
U.S. Pat. 4,608,251
U.S. Pat. 4,797,368
U.S. Pat. 5,139,941
U.S. Pat. 5,578,832
U.S. Pat. 5,861,242
U.S. Pat. 5,994,131
U.S. Pat. 6,406,921
U.S. Pat. 6,457,809
Abbondanzo, *Ann. Diagn. Pathol.*, 3(5):318-327, 1999.
Aitken et al., *Biochem. Soc. Trans.*, 30(4):351-360, 2002.
Aitken et al., *Nature*, 344(6267):594, 1990.
Aitken et al., *Trends Biochem. Sci.*, 17:498-501, 1992.
Aitken, *Trends Cell Biol.*, 6(9):341-347, 1996.
Albertson, *Breast Cancer Res. Treat.*, 78(3):289-298, 2003.
Allred et al., *Arch Surg*, 125(1):107-13, 1990.
Bernard and Wittwer, *Clinical Chemistry*, 48:1178-1185, 2002.
Boussif et al., *Proc. Natl. Acad. Sci. USA*, 92(16):7297-7301, 1995.
Brown et al. *Immunol. Ser.*, 53:69-82, 1990.
Brunet et al., *Cell*, 96(6):857-868, 1999.
Caley et al., *J. Virology*, 71(4):3031-3038, 1997.
Cantley, *Science*, 296:1655-1657, 2002.
Chan et al., *Biochem. Biophys. Res. Commun.*, 270(2):581-587, 2000.
Chang et al., *Hepatology*, 14:134A, 1991.
Chen and Okayama, *Mol. Cell Biol.*, 7(8):2745-2752, 1987.
Coffin, In: *Virology*, Fields et al. (Eds.), Raven Press, N.Y., 1437-1500, 1990.
Couch et al., *Am. Rev. Resp. Dis.*, 88:394-403, 1963.
Davis et al, *Curr. Biol.*, 6:146-148, 1996.
De Valck et al., *Biochem. Biophys. Res. Commun.*, 238(2):590-594, 1997.
Elbashir et al., *Methods*, 26:199-213, 2002.
Fechheimer et al., *Proc. Natl. Acad. Sci. USA*, 84:8463-8467, 1987.
Ferguson et al., *Proc. Natl. Acad. Sci. USA*, 97(11):6049-6054, 2000.
Fodor et al., *Biochemistry*, 30(33):8102-8108, 1991.
Forbes, *Semin. Oncol.*, 24(1 Suppl 1):S1-5-S1-19; S20-S35, 1997.

Fraley et al., *Proc. Natl. Acad. Sci. USA,* 76:3348-3352, 1979.
Fry et al., *Science,* 265(5175):1093-1095, 1994.
Gopal, *Mol. Cell. Biol.,* 5:1188-1190, 1985.
Graham and Prevec, *Biotechnology,* 20:363-390, 1992.
Graham and Van Der Eb, *Virology,* 52:456-467, 1973.
Graham et al, *J. General Virology,* 36:59-74, 1977.
Grunhaus et al., *Seminar in Virology,* 200(2):535-546, 1992.
Guthridge et al., *Mol. Cell,* 6(1):99-108, 2000.
Hacia et al., *Nature Genet.,* 14:441-449, 1996.
Harland and Weintraub, *J. Cell Biol.,* 101:1094-1099, 1985.
Hermeking et al., *Mol. Cell,* 1(1):3-11, 1997.
Horwich et al., *J. Virology,* 64:642-650, 1990.
Ichimura et al., *J. Neurochem.,* 56(4):1449-1451, 1991.
Ichimura et al., *Proc. Natl. Acad. Sci. USA,* 85(19):7084-7088, 1988.
Isobe et al., *J. Mol. Biol.,* 217(1):125-132, 1991.
Jones and Shenk, *Cell,* 13:181-188, 1978.
Kallionieemi et al., *Science,* 258(5083):818-821, 1992.
Kerr et al., *Br. J. Cancer,* 26(4):239-257, 1972.
Konigshoff et al., *Clinical Chemistry,* 49:219-229, 2003.
Laughlin et al., *J. Virol.,* 60(2):515-524, 1986.
Lebkowski et al., *Mol. Cell. Biol.,* 8(10):3988-3996, 1988.
Liu et al., *J. Biol. Chem.,* 271(24):14591-14595, 1996.
Liu et al., *Nature,* 376(6536):191-194, 1995.
MacBeath and Schreiber, *Science,* 289:1760-1763, 2000.
Masters and Fu, *J. Biol. Chem.,* 276(48):45193-45200, 2001.
McLaughlin et al., *J. Virol.,* 62(6):1963-1973, 1988.
Moore and Perez, In: *Physiological and biochemical aspects of nervous integration,* Carlson (Ed.,) 343-359, Prentice-Hall, N.J., 1967.
Munday et al., *Blood,* 96(2):577-584, 2000.
Muzyczka, Curr. *Topics Microbiol. Immunol.,* 158:97-129, 1992.
Nicolau and Sene, *Biochim. Biophys. Acta,* 721:185-190, 1982.
Pandey and Mann, *Nature,* 405:837-846, 2000.
PCT Appln. WO 84/03564
Pease et al., *Proc. Natl. Acad. Sci. USA,* 91:5022-5026, 1994.
Pelletier and Sonenberg, *Nature,* 334:320-325, 1988.
Pinkel et al., *Nat. Genet.,* 20(2):207-211,.1998.
Pollack et al., *Nat. Genet.,* 23(1):41-46, 1999.
Potter et al., *Proc. Natl. Acad. Sci. USA,* 81:7161-7165, 1984.
Remington's Pharmaceutical Sciences, 15th ed., pages 1035-1038 and 1570-1580, Mack Publishing Company, Easton, Pa., 1980.
Renan, *Radiother. Oncol.,* 19:197-218, 1990.
Ries et al., *Clin. Cancer Res.,* 5(5):1115-1124, 1999.
Rippe et al., *Mol. Cell Biol.,* 10:689-695, 1990.
Rittinger et al., *Mol. Cell,* 4:153-166, 1999.
Rogers et al., *Eur. J. Surg. Oncol.,* 28(5):467-478, 2002.
Rosenquist et al., *J. Mol. Evol.,* 51(5):446-458, 2000.
Roux et al., *Proc. Natl. Acad. Sci. USA,* 86:9079-9083, 1989.
Shin et al., *Biochem. Biophys. Res. Commun.,* 246(2):313-319, 1998.
Shoemaker et al., *Nature Genet.,* 14:450-456, 1996.
Snijders et al., *Mol. Pathol.,* 53(6):289-294, 2000.
Solinas-Toldo et al., *Genes Chromosomes Cancer,* 20(4):399-407, 1997.
Sondik, *Cancer,* 74(3 Suppl):995-999, 1994.
Tan et al., *Mol. Cell,* 9:993-1004, 2002.
Toker et al., *Eur. J. Biochem.,* 191(2):421-429, 1990.
Top et al., *J. Infect. Dis.,* 124:155-160, 1971.
Tratschin et al., *Mol. Cell. Biol.,* 4:2072-2081, 1984.
Tur-Kaspa et al., *Mol. Cell Biol.,* 6:716-718, 1986.
Veltman et al., *Cancer Res.,* 63(11):2872-2880, 2003.
Vercoutter-Edouart et al., *Cancer Res.,* 61(1):76-80, 2001.
Vivanco and Sawyers, *Nat. Rev. Cancer,* 2:489-501, 2002.
Wajant, *Science,* 296:1635-1636, 2002.
Walker, *Science,* 296:557-559, 2002.
Wang and Shakes, *J. Mol. Evol.,* 43(4):384-398, 1996.
Wang et al., *Anal. Chem.,* 72(21):5285-5289, 2000.
Watanabe et al., *Brain Res. Mol. Brain Res.,* 10(2):151-158, 1991.
Welch and Wei, *Endocrine-Related Cancer,* 5:155-197, 1998.
Wu and Wu, *Biochemistry,* 27:887-892, 1988.
Wu and Wu, *J. Biol. Chem.,* 262:4429-4432, 1987.
Xiao et al., *Nature,* 376(6536):188-191, 1995.
Yaffe, *FEBS Lett.,* 513(1):53-57, 2002.
Yang et al. *Cancer Res.,* 61:8150-8157, 2001.
Yang et al., *Molec. Pharmacol.,* 61:269-276, 2002.
Yang et al., *Proc Natl. Acad. Sci. USA,* 87:9568-9572, 1990.
Zha et al., *Cell,* 87(4):619-628, 1996.
Zhang et al., *Proc. Natl. Acad. Sci. USA,* 96(15):8511-8515, 1999.

What is claimed is:

1. A method of determining prognosis in a subject with breast cancer, comprising determining overexpression of 14-3-3 zeta protein (SEQ ID NO:1) in a breast tumor sample from said subject relative to expression of 14-3-3 zeta protein in breast tissue from a subject that does not have breast cancer, wherein said overexpression of 14-3-3 zeta protein indicates that said subject with breast cancer has a lower survival rate as compared to a subject with a breast cancer that does not overexpress 14-3-3 zeta protein.

2. The method of claim 1, wherein the subject with breast cancer is a human.

3. The method of claim 1, wherein determining expression of 14-3-3 zeta protein is measured by western blot analysis, immunohistochemistry, and/or protein array.

4. The method of claim 1, wherein the breast cancer is metastatic breast cancer.

5. The method of claim 3, wherein determining expression of 14-3-3 zeta protein is measured by western blot analysis.

6. The method of claim 3, wherein determining expression of 14-3-3 zeta protein is measured by immunohistochemistry.

7. The method of claim 3, wherein determining expression of 14-3-3 zeta protein is measured by protein array.

8. A method of diagnosing breast cancer, lung cancer, liver cancer, uterine cancer, or stomach cancer in a subject, comprising determining overexpression of 14-3-3 zeta protein (SEQ ID NO:1) in a breast, lung, liver, uterine, or stomach tissue test sample, respectively, from said subject relative to expression of 14-3-3 zeta protein in breast, lung, liver, uterine, or stomach tissue control sample from a subject that does not have breast cancer, lung cancer, liver cancer, uterine cancer, or stomach cancer, respectively, wherein said overexpression of 14-3-3 zeta protein indicates that the patient from which the test sample was obtained has breast cancer, lung cancer, liver cancer, uterine cancer, or stomach cancer, respectively.

9. The method of claim 8, wherein the subject is a human.

10. The method of claim 8, wherein determining overexpression of 14-3-3 zeta protein is measured by western blot analysis, immunohistochemistry, and/or protein array.

11. The method of claim 10, wherein determining expression of 14-3-3 zeta protein is measured by western blot analysis.

12. The method of claim 10, wherein determining expression of 14-3-3 zeta protein is measured by immunohistochemistry.

13. The method of claim 10, wherein determining expression of 14-3-3 zeta protein is measured by protein array.

14. The method of claim 8, wherein the method is a method of diagnosing breast cancer, wherein the tissue test sample is breast tissue.

15. The method of claim 8, wherein the method is a method of diagnosing lung cancer, wherein the tissue test sample is lung tissue.

16. The method of claim 8, wherein the method is a method of diagnosing liver cancer, wherein the tissue test sample is liver tissue.

17. The method of claim 8, wherein the method is a method of diagnosing uterine cancer, wherein the tissue test sample is uterine tissue.

18. The method of claim 8, wherein the method is a method of diagnosing stomach cancer, wherein the tissue test sample is stomach tissue.

* * * * *